US012660769B2

(12) United States Patent
Dawe et al.

(10) Patent No.: US 12,660,769 B2
(45) Date of Patent: Jun. 23, 2026

(54) HETEROZYGOUS CENH3 MONOCOTS AND METHODS OF USE THEREOF FOR HAPLOID INDUCTION AND SIMULTANEOUS GENOME EDITING

(71) Applicants:University of Georgia Research Foundation, Inc., Athens, GA (US); Cold Spring Harbor Laboratory, Cold Spring Harbor, NY (US)

(72) Inventors: R. Kelly Dawe, Athens, GA (US); David Jackson, Brooklyn, NY (US)

(73) Assignees: University of Georgia Research Foundation, Inc., Athens, GA (US); Cold Spring Harbor Laboratory, Cold Spring Harbor, NY (US)

( * ) Notice: Subject to any disclaimer, the term of this patent is extended or adjusted under 35 U.S.C. 154(b) by 402 days.

(21) Appl. No.: 18/001,370

(22) PCT Filed: Jun. 9, 2021

(86) PCT No.: PCT/US2021/036605
§ 371 (c)(1),
(2) Date: Dec. 9, 2022

(87) PCT Pub. No.: WO2021/252619
PCT Pub. Date: Dec. 16, 2021

(65) Prior Publication Data
US 2023/0270067 A1 Aug. 31, 2023

Related U.S. Application Data

(60) Provisional application No. 63/036,902, filed on Jun. 9, 2020, provisional application No. 63/036,910, filed on Jun. 9, 2020.

(51) Int. Cl.
| | |
|---|---|
| *A01H 1/08* | (2006.01) |
| *C07K 14/415* | (2006.01) |
| *C12N 9/22* | (2006.01) |
| *C12N 15/11* | (2006.01) |
| *C12N 15/82* | (2006.01) |
| *C12Q 1/6895* | (2018.01) |

(52) U.S. Cl.
CPC ............. *A01H 1/08* (2013.01); *C07K 14/415* (2013.01); *C12N 9/22* (2013.01); *C12N 15/11* (2013.01); *C12N 15/8213* (2013.01); *C12Q 1/6895* (2013.01); *C12N 2310/20* (2017.05); *C12N 2800/80* (2013.01); *C12Q 2600/13* (2013.01)

(58) Field of Classification Search
CPC .......... A01H 1/08; C07K 14/415; C12N 9/22; C12N 15/11; C12N 15/8213; C12N 2310/20; C12N 2800/80; C12Q 1/6895; C12Q 2600/13
See application file for complete search history.

(56) References Cited

U.S. PATENT DOCUMENTS

| | | | |
|---|---|---|---|
| 5,356,802 | A | 10/1994 | Chandrasegaran |
| 5,436,150 | A | 7/1995 | Chandrasegaran |
| 5,487,994 | A | 1/1996 | Chandrasegaran |
| 6,140,081 | A | 10/2000 | Barbas |
| 6,453,242 | B1 | 9/2002 | Eisenberg |
| 6,534,261 | B1 | 3/2003 | Coxiii |
| 6,610,512 | B1 | 8/2003 | Barbas |
| 6,717,034 | B2 | 4/2004 | Jiang |
| 6,746,838 | B1 | 6/2004 | Choo |
| 6,866,997 | B1 | 3/2005 | Choo |
| 7,067,617 | B2 | 6/2006 | Barbasiii |
| 8,618,354 | B2 | 12/2013 | Chan |
| 10,285,348 | B2 * | 5/2019 | Kelliher .................. A01H 1/08 |
| 10,954,523 | B2 | 3/2021 | Kelliher |
| 2002/0165356 | A1 | 11/2002 | Barbas |
| 2004/0197892 | A1 | 10/2004 | Moore |

(Continued)

FOREIGN PATENT DOCUMENTS

| | | |
|---|---|---|
| CN | 106755077 A | 5/2017 |
| CN | 109982560 A | 7/2019 |

(Continued)

OTHER PUBLICATIONS

Yoon et al (2022). The Plant Genome, 16(2), e20209. (Year: 2022).*
Elisafenko et al (2021). BMC Plant Biology. 21:541. (Year: 2021).*
Karimi-Ashtiyani et al (2015). PNAS, 112(36):11211-11216. (Year: 2015).*
Britt et al (2016). Front. Plant Sci. 7:357. (Year: 2016).*
Lermontova et al (2011). The Plant Journal. 68:40-50. (Year: 2011).*
Kelliher et al (2016 ). Frontiers in Plant Science. 7:414. (Year: 2016).*
Kuppu et al (2020) Plant Biotechnology Journal. 18:2068-2080. (Year: 2020).*

(Continued)

*Primary Examiner* — Bratislav Stankovic
(74) *Attorney, Agent, or Firm* — Pabst Patent Group LLP

(57) ABSTRACT

Monocot plants heterozygous for centromeric histone 3 (CenH3) and optionally expressing gene editing constructs, for use in inducing haploids of a monocot target plant and optionally pass-through gene editing are provided. The monocot haploid inducer plants are typically composed of diploid plant cells having only one allele encoding a functional CENH3 protein. The diploid plant cells can also include, for example, one CenH3 allele encoding non-functional CENH3 protein. In some embodiments, the allele encoding non-functional CENH3 protein is a frameshift mutation, protein null allele, an RNA null allele, or a combination thereof. The monocot haploid inducer plant can also include gene editing machinery, such as a site-directed nuclease and optionally a guide RNA stably expressed by cells of the monocot plant. Methods of inducing formation of a target haploid monocot plant while optionally simultaneously modifying the target monocot plant's genome are also provided.

19 Claims, 8 Drawing Sheets

Specification includes a Sequence Listing.

(56)                    References Cited

U.S. PATENT DOCUMENTS

| | | | |
|---|---|---|---|
| 2005/0064474 | A1 | 3/2005 | Urnov |
| 2006/0188987 | A1 | 8/2006 | Guschin |
| 2007/0154989 | A1 | 7/2007 | Barbas |
| 2007/0213269 | A1 | 9/2007 | Barbas |
| 2008/0131962 | A1 | 6/2008 | Miller |
| 2011/0145940 | A1 | 6/2011 | Voytas |
| 2014/0090099 | A1 | 3/2014 | Chan |
| 2015/0201619 | A1 | 7/2015 | Annigeri |
| 2018/0116141 | A1 | 5/2018 | Kuppu |
| 2018/0139917 | A1* | 5/2018 | Bolduan ................ A01H 1/021 |
| 2018/0327785 | A1 | 11/2018 | Cigan |
| 2018/0332790 | A1 | 11/2018 | Kelliher et al. |
| 2019/0225657 | A1* | 7/2019 | Op Den Camp .... A01H 6/4636 |
| 2019/0343060 | A1 | 11/2019 | Chan |
| 2020/0060110 | A1 | 2/2020 | Kelliher et al. |

FOREIGN PATENT DOCUMENTS

| | | | | |
|---|---|---|---|---|
| RU | 2571927 | C2 | 12/2015 | |
| WO | 1998053059 | | 11/1998 | |
| WO | 2003016496 | | 2/2003 | |
| WO | 2007014275 | | 2/2007 | |
| WO | 2009137135 | | 11/2009 | |
| WO | 2012094307 | A2 | 7/2012 | |
| WO | 2013176772 | | 11/2013 | |
| WO | 2014018423 | | 1/2014 | |
| WO | 2016102665 | A2 | 6/2016 | |
| WO | 2017004375 | | 1/2017 | |
| WO | 2017200386 | | 11/2017 | |
| WO | 2018052919 | A1 | 3/2018 | |
| WO | 2018102816 | A1 | 6/2018 | |
| WO | 2019136417 | | 7/2019 | |
| WO | 2020073963 | | 4/2020 | |
| WO | WO-2020073963 | A1 * | 4/2020 | ........... A01H 6/4678 |
| WO | 2020131788 | | 6/2020 | |

OTHER PUBLICATIONS

Barkan and Martienssen, "Inactivation of maize transposon Mu suppresses a mutant phenotype by activating an outward-reading promoter near the end of Mu1", Proc. Natl. Acad. Sci. U.S. A., 88(8):3502-3506 (1991).
Beerli and Barbas, "Engineering polydactyl zinc-finger transcription factors", Nature Biotechnol., 20:135-141 (2002).
Birchler, et al., "Engineered minichromosomes in plants", Current Opinion in Plant Biology, 19:76-80 (2014).
Black and Bassett, "The histone variant CENP-A and centromere specification", Curr. Opin. Cell Biol., 20(1):91-100 (2008).
Britt and Kuppu, "Cenh3: An Emerging Player in Haploid Induction Technology", Frontiers in Plant Science, 7:357, (2016).
Ceccaldi, et al., "Repair Pathway Choices and Consequences at the Double-Strand Break", Trends Cell Biol., 26(1):52-64 (2016).
Cermak et al., "Efficient design and assembly of custom TALEN and other TAL effector-based constructs for DNA targeting", Nucl Acids Res, 39(17):7879 (2011).
Cermak, et al., "A Multipurpose Toolkit to Enable Advanced Genome Engineering in Plants", Plant Cell, 29(6):1196-1217 (2017).
Chaikam et al., "Doubled haploid technology for line development in maize: technical advances and prospects", TAG Theoretical and applied genetics Theoretische Und Angewandte Genetik, 132(12):3227-43 (2019).
Chase, "Monoploids and Monoploid-Derivatives of Maize (Zea mays L.)", Bot. Rev., 35(2):117-168 (1969).
Cheeseman and Desai, "Molecular architecture of the kinetochore-microtubule interface", Nature Reviews Molecular Cell Biology, 9:33-46 (2008).
Choo et al., "Advances in zinc finger engineering", Curr. Opin. Struct. Biol., 10(4):411-416 (2000).
Coe, "A Line of Maize with High Haploid Frequency", The American Naturalist, 93(873):381-82 (1959).
Comai and Tan, "Haploid induction and genome instability", Trends in Genetics, 35(11):791-803 (2019).

Cong et al., "Multiplex genome engineering using CRISPR/Cas systems", Science, 15;339(6121):819-823 (2013).
Copenhaver and Preuss, "Haploidy with histones", Nat. Biotechnol., 28(5): 423-424 (2010).
Eid, et al., "CRISPR base editors: genome editing without double-stranded breaks", Biochem J, 475(11):1955-1964 (2018).
Evans, "The indeterminate gametophyte1 gene of maize encodes a LOB domain protein required for embryo Sac and leaf development", Plant Cell, 19(1):46-62 (2007).
Feng, et al., "The deposition of CENH3 in maize is stringently regulated", Plant J., 102(1):6-17 (2019).
Gaudelli et al., "Programmable base editing of A•T to G•C in genomic DNA without DNA cleavage", Nature, 551(7681):464-471 (2017).
Gilles et al., "Loss of pollen_specific phospholipase Not Like Dad triggers gynogenesis in maize", The EMBO Journal, 36(6):707-17 (2017).
Gordon-Kamm et al., "Transformation of Maize Cells and Regeneration of Fertile Transgenic Plants", Plant Cell, 2(7):603-618 (1990).
Haughn and chaudhury, "A genetic analysis of seed coat development in Arabidopsis", Trends Plant Sci., 10(10):472-7 (2005).
He, et al., "Self-cleaving ribozymes enable the production of guide RNAs from unlimited choices of promoters for CRISPR/Cas9 mediated genome editing", J Genet Genomics, 20;44(9): 469-472 (2017).
Howman, et al., "Early Disruption of Centromeric Chromatin Organization in Centromere Protein A (Cenpa) Null Mice." Proceedings of the National Academy of Sciences of the United States of America, 97 (3): 1148-53 (2005).
Hu et al., "The Genetic Basis of Haploid Induction in Maize Identified with a Novel Genome-Wide Association Method", Genetics, 202(4):1267-76 (2016).
Isalan et al., "A rapid, generally applicable method to engineer zinc fingers illustrated by targeting the HIV-1 promoter", Nature Biotechnol., 19(7):656-660 (2001).
Ishida et al., "High efficiency transformation of maize (Zea mays L.) mediated by Agrobacterium tumefaciens," Nature Biotechnol, 14:745-750 (1996).
Ishii, et al., "Haploidization via Chromosome Elimination: Means and Mechanisms", Annu. Rev. Plant Biol., 67, 421-438 (2016).
Jaganathan, et al., "CRISPR for Crop Improvement: An Update Review", Front. Plant Sci., 9:985 (2018).
Jinek, et al., "A Programmable Dual-RNA-Guided DNA Endonuclease in Adaptive Bacterial Immunity", Science, 337(6096):816-21 (2012).
Kalinowska et al., "State_of_ the_art and novel developments of in vivo haploid technologies", Tag. Theoretical and Applied Genetics. Theoretische Und Angewandte Genetik, 132(3): 593-605 (2019).
Karimi-Ashtiyani et al., "Point mutation impairs centromeric CENH3 loading and induces haploid plants", Proc. Natl. Acad. Sci. U.S. A, 112(36):11211-16 (2015).
Kelliher et al., "Matrilineal, a sperm-specific phospholipase, triggers maize haploid induction", Nature, 542(7639):105-9, (2017).
Kelliher, et al., "Maternal Haploids Are Preferentially Induced by CENH3-tailswap Transgenic Complementation in Maize", Front. Plant Sci. 7, 414 (2016).
Kelliher, et al., "One-step genome editing of elite crop germplasm during haploid induction", Nat. Biotechnol., 37(3): 287-292 (2019).
Khanday, et al., "A male-expressed rice embryogenic trigger redirected for asexual propagation through seeds", Nature 565, 91-95 (2019).
Kim and Chandrasegaran, "Chimeric Restriction Endonuclease", Proc. Natl. Acad. Sci. USA, 91:883-887 (1994a).
Kim et al., "Insertion and deletion mutants of FokI restriction endonuclease", J. Biol. Chem., 269(50):31978-31982 (1994b).
Komor et al., "Improved base excision repair inhibition and bacteriophage Mu Gam protein yields C:G-to-T:A base editors with higher efficiency and product purity", Science Advances, 3(8):eaao4774 (2017).
Komor et al., "Programmable editing of a target base in genomic DNA without double-stranded DNA cleavage", Nature, 533(7603):420-424 (2016).

(56)　　　　　References Cited

OTHER PUBLICATIONS

Kuppu et al., "Point Mutations in Centromeric Histone Induce Post-zygotic Incompatibility and Uniparental Inheritance", PLoS Genetics, 11(9):e1005494 (2015).

Kuppu, et al., "A Variety of Changes, Including CRISPR/Cas9-mediated Deletions, in CENH3 Lead to Haploid Induction on Outcrossing", Plant Biotechnol J, 18(10):2068-2080 (2020).

Lee, et al., "Activities and specificities of CRISPR/Cas9 and Cas12a nucleases for targeted mutagenesis in maize", Plant Biotechnology, 17(2):362-372 (2019).

Lermontova et al., "Knockdown of CENH3 in *Arabidopsis* reduces mitotic divisions and causes sterility by disturbed meiotic chromosome segregation", The Plant Journal, 68(1): 40-50 (2006).

Lermontova, et al., "Loading of *Arabidopsis* Centromeric Histone CENH3 Occurs Mainly during G2 and Requires the Presence of the Histone Fold Domain", Plant Cell, 18(10):2443-2451 (2006b).

Li and Durbin, "Fast and accurate short read alignment with Burrows-Wheeler transform", Bioinformatics, 25(14):1754-1760 (2009).

Li et al., "Alteration of the cleavage distance of Fok I restriction endonuclease by insertion mutagenesis", Proc. Natl. Acad. Sci. USA, 90:2764-2768 (1993).

Li et al., "Functional domains in Fok I restriction endonuclease", Proc., Natl. Acad. Sci. USA 89:4275-4279 (1992).

Li, et al., "Precise gene replacement in rice by RNA transcript-templated homologous recombination", Nature Biotechnology, 37(4):445-450 (2019).

Liang et al., "Targeted Mutagenesis in *Zea mays* Using TALENs and the CRISPR/Cas System", J Genet Genom, 41(2):63-68, (2014).

Lipikhina, et al., "Chromosomal assignment of centromere-specific histone CENH3 genes in rye (*Secale cereale* L.) and their phylogeny", Comp Cytogenet., 14;11(4):821-832 (2017).

Liu et al., "A 4-bp Insertion at ZmPLA1 Encoding a Putative Phospholipase A Generates Haploid Induction in Maize", Molecular Plant, 10(3):520-22 (2017).

Lowder, et al., "A CRISPR/Cas9 Toolbox for Multiplexed Plant Genome Editing and Transcriptional Regulation", Plant Physiol., 169(2):971-985 (2015).

Lowe, et al., "Morphogenic Regulators Baby boom and Wuschel Improve Monocot Transformation", The Plant Cell, 28(9):1998-2015 (2016).

Maheshwari, et al., "Naturally Occurring Differences in CENH3 Affect Chromosome Segregation in Zygotic Mitosis of Hybrids", PLoS Genet., 11: el004970 (2015).

Marimuthu, et al., "Synthetic clonal reproduction through seeds", Science, 331(6019):876 (2011).

Martin, et al., "Cutadapt Removes Adapter Sequences From High-Throughput Sequencing Reads", EMBnet.journal, 17:1 (2011).

Miller et al., "A TALE nuclease architecture for efficient genome editing", Nature Biotechnol., 29:143-148, (2011).

Miller, et al., "An improved zinc-finger nuclease architecture for highly specific genome editing", Nature Biotechnology, 25:778-785(2007).

Pabo et al., "Design and selection of novel Cys2His2 zinc finger proteins", Ann. Rev. Biochem., 70:313-340 (2001).

Panchenko, et al., "Replacement of histone H3 with CENP-A directs global nucleosome array condensation and loosening of nucleosome superhelical termini", 108(40):16588-16593 (2011).

Paz, et al., "Assessment of conditions affecting Agrobacterium-mediated soybean transformation using the cotyledonary node explant", Euphytica, 136:167-179 (2004).

Prigge et al., "New Insights into the Genetics of in Vivo Induction of Maternal Haploids, the Backbone of Doubled Haploid Technology in Maize", Genetics, 190(2):781-93 (2012).

Puchta, "Using CRISPR/Cas in three dimensions: towards synthetic plant genomes, transcriptomes and epigenomes", The Plant Journal, 87:5-15 (2016).

Ravi and Chan, "Haploid plants produced by centromere-mediated genome elimination", Nature, 464(7288):615-18 (2010).

Ravi, et al., "A haploid genetics toolbox for *Arabidopsis thaliana*", Nature Communications, 5:5334 (2014).

Ravi, et al., "Meiosis-Specific Loading of the Centromere-Specific Histone CENH3 in *Arabidopsis thaliana*", PLoS Genet., 7(6):e1002121 (2011).

Ravi, et al., "The rapidly evolving centromere-specific histone has stringent functional requirements in *Arabidopsis thaliana*", Genetics, 186(2):461-71 (2010).

Roberts et al., "REBASE: restriction enzymes and methyltransferases", Nucleic Acids Res., 31(1):418-420 (2003).

Rodriguez-Leal, et al., "Engineering Quantitative Trait Variation for Crop Improvement by Genome Editing", Cell, 171(2):470-80 (2017).

Sander et al., "Selection-free zinc-finger-nuclease engineering by context-dependent assembly (CoDA)", Nature Met, 8(1):67-69, (2011).

Sanei, et al., "Loss of centromeric histone H3 (CENH3) from centromeres precedes uniparental chromosome elimination in interspecific barley hybrids", Proc. Natl. Acad. Sci. U. S. A., 108:E498-505 (2011).

Segal and Barbas, "Custom DNA-binding proteins come of age: polydactyl zinc-finger proteins", Curr. Opin. Biotechnol., 12(6):632-637 (2001).

Shi, et al., "ARGOS8 variants generated by CRISPR-Cas9 improve maize grain yield under field drought stress conditions", Plant Biotechnology Journal, 15(2):207-216 (2017).

Shukla, et al., "Precise genome modification in the crop species *Zea mays* using zinc-finger nucleases", Nature, 459(7245): 437-441(2009).

Stoler, et al., "A Mutation in CSE4, an Essential Gene Encoding a Novel Chromatin-Associated Protein in Yeast, Causes Chromosome Nondisjunction and Cell Cycle Arrest at Mitosis", Genes & Development 9(5):573-86.

Sturaro, et al., "Cloning and Characterization of GLOSSY1, a Maize Gene Involved in Cuticle Membrane and Wax Production", Plant Physiol., 138(1):478-489 (2005).

Svitashev, et al., "Targeted Mutagenesis, Precise Gene Editing, and Site-Specific Gene Insertion in Maize Using Cas9 and Guide RNA", Plant Physiology, 169(2):931-945 (2015).

Taguchi-Shiobara, et al., "The fasciated ear2 gene encodes a leucine-rich repeat receptor-like protein that regulates shoot meristem proliferation in maize", Genes Dev., 15(20): 2755-2766 (2001).

Tan, et al., "Catastrophic chromosomal restructuring during genome elimination in plants", Elife 4:e06516 (2015).

Tang, et al., "A large-scale whole-genome sequencing analysis reveals highly specific genome editing by both Cas9 and Cpf1 (Cas12a) nucleases in rice", Genome Biology, 19(84) (2018).

Thorvaldsdóttir, et al., "Integrative Genomics Viewer (IGV): high-performance genomics data visualization and exploration", Brief Bioinform. 14(2), 178-192 (2013).

Wang and Dawe, "Centromere Size and Its Relationship to Haploid Formation in Plants", Molecular Plant, 11(3):398-406 (2018).

Wang, et al., "Fixation of hybrid vigor in rice: synthetic apomixis generated by genome editing", aBIOTECH, 1(2): 15-20 (2020).

Xu, et al., "Sequence analysis of the cloned glossy8 gene of maize suggests that it may code for a β-ketoacyl reductase required for the biosynthesis of cuticular waxes", Plant Physiology, 115(2):501-510 (1997).

Xue and Greene, "DNA Repair Pathway Choices in CRISPR-Cas9-Mediated Genome Editing", Trends in Genetics, 37(7):639-656 (2021).

Yao et al., "OsMATL mutation induces haploid seed formation in indica rice", Nature Plants, 4(8):530-33 (2018).

Zhang et al., "The emerging and uncultivated potential of CRISPR technology in plant science", Nat Plants, 5(8): 778-794 (2019).

Zhao, et al., "Gene Expression and Chromatin Modifications Associated with Maize Centromeres", G3 (Bethesda), 6(1):183-92 (2015).

Zhong, et al., "A DMP-triggered in vivo maternal haploid induction system in the dicotyledonous *Arabidopsis*", Nat Plants, 6(5):466-472 (2020).

International Search Report received for PCT Patent Application No. PCT/US2021/036605, mailed on Oct. 18, 2021, 4 pages.

Wang , et al., "Haploid induction by a maize cenh3 null mutant", Sci Adv., vol. 7, No. 4; eabe2299, Jan. 20, 2021, 7 pages.

(56)               References Cited

OTHER PUBLICATIONS

Nakamura, et al., "Codon usage tabulated from international DNA sequence databases: status for the year 2000", Nucleic Acids Res, vol. 28, No. 1, Jan. 1, 2000, p. 292.

\* cited by examiner

5'-CCAGGGACTGTAGCGCTGCGGGA-3'
3'-GGTCCCTGACATCGCGACGCCCT-5'
    PAM        sgRNA

TGGCGGCCAGGGACTGTAGCGCTGCGG   WILD TYPE
TGGCGGCCAGGG-CTGTAGCGCTGCGG   MUTANT

DIPLOID

HAPLOID

PHENOTYPE REFERENCE FROM
FROM TAGUCHI-SHIOBARA ET AL

PHENOTYPE REFERENCE FROM
FROM TAGUCHI-SHIOBARA ET AL

EAR OF HAPLOID fea2-CR4 PLANT

HETEROZYGOUS CENH3 MONOCOTS AND METHODS OF USE THEREOF FOR HAPLOID INDUCTION AND SIMULTANEOUS GENOME EDITING

CROSS-REFERENCE TO RELATED APPLICATIONS

This application is a National Phase application under 35 U.S.C. § 371 of PCT/US2021/036605, filed Jun. 9, 2021, which claims the benefit of and priority to U.S. Ser. No. 63/036,902 filed Jun. 9, 2020, and U.S. Ser. No. 63/036,910 filed Jun. 9, 2020, each of which is incorporated by reference in its entirety.

STATEMENT REGARDING FEDERALLY SPONSORED RESEARCH

This invention was made with government support under 1444514 awarded by the National Science Foundation. The Government has certain rights in the invention.

REFERENCE TO SEQUENCE LISTING

The Sequence Listing submitted as a text file named "UGA_2020_139_03_PCT_ST25.txt," created on Jun. 7, 2021, and having a size of 20,835 bytes is hereby incorporated by reference pursuant to 37 C.F.R § 1.52(e)(5).

FIELD OF THE INVENTION

The field of the invention is generally related to haploid inducer plant lines, and methods of use thereof for creating genetically modified doubled haploid plants.

BACKGROUND OF THE INVENTION

Tens of thousands of maize haploid lines are generated by breeding companies around the world each year as a prerequisite for creating new inbreds, which are ultimately used to create hybrids for sale. The induced haploids are doubled by chemical treatment and immediately tested for agronomic performance. The enabling technology was the discovery of a maize inbred called Stock 6 that induces haploids when crossed as a male (Coe, et al., *The American Naturalist,* 93 (873): 381-82 (1959)). About 3% of the progeny from this cross are haploid for the maternal genome. This line has now been improved and selected for improved haploid formation, which can range from 3-20% (Hu et al., *Genetics,* 202 (4): 1267-76 (2016); Prigge et al., *Genetics,* 190 (2): 781-93 (2012)). All maize haploid-inducing applications trace to this original discovery and breeding lines derived from it. The relevant literature on this topic has been heavily reviewed (Chaikam et al., TAG. *Theoretical and Applied Genetics. Theoretische Und Angewandte Genetik,* 132 (12): 3227-43 (2019); Comai and Tan, *Trends in Genetics.* doi: 10.1016/j.tig.2019.07.005 (2019); Kalinowska et al., TAG. *Theoretical and Applied Genetics. Theoretische Und Angewandte Genetik,* 132 (3): 593-605 (2019)). The gene responsible for Stock 6-based haploid induction (Matrilineal, or matl) is a patatin-like phospholipase expressed primarily in pollen (Kelliher et al., *Nature,* 542 (7639): 105-9 (2017); Liu et al., *Molecular Plant,* 10 (3): 520-22 (2017); Gilles et al., *The EMBO Journal,* 36 (6): 707-17 (2017)). Its mechanism of action is not understood, but may involve a change in membrane properties during fertilization that leads to sudden loss of the paternal genotype. Mutations in matl also induce haploids in rice (Yao et al., *Nature Plants,* 4 (8): 530-33 (2018)), indicating that this method of haploid induction may be broadly used for monocot crop species.

Haploid induction itself is of broad interest. Also important was the subsequent demonstration that matl can be used to "invisibly" pass a CRISPR/Cas9 cassette into any inbred background (Kelliher et al., *Nature Biotechnology,* 37 (3): 287-92 (2019)) and edit genes in more than 3% of the haploid progeny. The resulting haploids can then be doubled to create inbreds with homozygous mutations in a fast, GMO-free manner. Any other way of editing genes needs transformation and regeneration; a process that is heavily genotype-dependent. By using a genotype-independent haploid inducer, this bottleneck can be avoided. However, the method is cumbersome, as it needs creating a mutation in matl before commencing with gene editing at another site. Lines containing the matl mutation are also unhealthy and difficult to propagate. Further, since the mechanism of matl action is not known, it is not clear how Cas9 is able to gain access to the maternal genome. Since the mechanism is not known, it is difficult to improve the technology.

Another method of inducing haploids is centromere-mediated haploid induction (Ravi and Chan (Ravi, et al., *Genetics,* 186 (2): 461-71 (2010), Ravi, et al., *PLoS Genet.,* 7(6):e1002121 (2011) doi: 10.1371/journal.pgen.1002121, Ravi et al., *Nature,* 464 (7288): 615-18 (2011)) found that a cenh3−/− *Arabidopsis* null mutant, when complemented with a modified version of CENH3 called "GFP-tailswap" can induce paternal haploids a high frequency (-25%). GFP-tailswap is a complex transgene with a substitution in the histone tail and large GFP moiety added to the N terminus. Other forms of tailswap involving CENH3 genes from different species with or without GFP (Britt and Kuppu, *Frontiers in Plant Science,* 7 (April): 357, (2016)), and point mutations that confer single amino acid changes of CENH3 can also induce haploids at a lower frequency (Karimi-Ashtiyani et al., *PNAS,* 112 (36): 11211-16 (2015); Kuppu et al., *PLoS Genetics,* 11 (9): e1005494 (2015), Kalinowska et al., TAG. *Theoretical and Applied Genetics. Theoretische Und Angewandte Genetik,* 132 (3): 593-605 (2019)).

Centromere mediated haploid induction has also been successful in several other dicot species (Kalinowska et al., TAG. *Theoretical and Applied Genetics. Theoretische Und Angewandte Genetik,* 132 (3): 593-605 (2019)). Results in monocots are limited and unreliable (Kelliher et al., *Frontiers in Plant Science,* 7 (March): 414 (2016)), leading to the general view that for monocots, the Matrilineal system will be used, and for dicots, centromere-mediated haploid induction (Kalinowska et al., TAG. *Theoretical and Applied Genetics. Theoretische Und Angewandte Genetik,* 132 (3): 593-605 (2019)).

Thus, there remains a need for improved compositions and methods for haploid induction in monocots and haploids formed therefrom, optionally in combination with simultaneous gene editing for induction of one or more mutations relative to the background genome.

SUMMARY OF THE INVENTION

Monocot plants heterozygous for centromeric histone 3 (CenH3) and use thereof in methods for efficient centromere-mediated haploid induction in a target plant are provided. The monocot haploid inducer plants are typically composed of diploid plant cells having only one CENH3 allele that is fully functional. The diploid plant cells can also include, for example, one CenH3 allele encoding nonfunctional CENH3 protein. In some embodiments, the allele encoding non-functional CENH3 protein is a protein null allele, an RNA null allele, or a combination thereof. In some embodiments, the endogenous CenH3 loci on a first diploid chromosome is mutated, or partially or completely deleted. In some embodiments, the mutation is frameshift mutation that introduces a stop codon, causing the gene to express a truncated, non-functional protein. Typically, the endogenous CenH3 loci on a second (i.e., the other) diploid chromosome is intact. The functional CENH3 protein can be wildtype CENH3 protein.

Typically, the plant lacks a chromosomally integrated or extrachromosomal transgene encoding wildtype CenH3, CENH3 protein variants, and fusion proteins. Thus, typically, the plant lacks a construct encoding a CENH3-green fluorescent protein (GFP) fusion protein such as GFP-tailswap. In some embodiments, the cenh3 null is used alone or in combination with other technologies that make use of haploids, such as synthetic apomixis, or transferring engineered chromosomes from one line to another.

The monocot haploid inducer plant can also optionally include gene editing machinery, such as a site-directed nuclease and optionally a guide RNA stably expressed by cells of the monocot plant. Typically constructs expressing the gene editing machinery (e.g., nuclease and optionally guide RNA) are stably expressed by the monocot plant. In some embodiments, the site directed nuclease is a CRISPR-based system, a transcription-activator like effector nuclease (TALEN), or a zinc-finger nuclease (ZFN), which may be deployed as cytidine deaminase or adenine deaminase fusion proteins. In some embodiments, a heterologous nucleic acid construct encoding the nuclease is integrated into the haploid inducer plant's genome.

In some embodiments, the monocot haploid inducer plant's genome includes a donor nucleic acid sequence to be introduced into a target plant's genome by homology-directed repair (HDR) following cleavage by the nuclease.

Also provided are egg and sperm cells formed by the haploid inducer plants, lacking the one allele encoding functional CENH3 protein, and expressing gene editing machinery. In some embodiments, the egg cells have no more than about 12.5% functional CENH3 protein relative to a corresponding egg cell formed by a CenH3 homozygous plant. In some embodiments, sperm cells have no more than about 25% functional CENH3 protein relative to a corresponding sperm cell formed by a CenH3 homozygous plant.

Methods of inducing formation of a target haploid monocot plant are also provided. The methods typically include pollinating a parent monocot target plant with pollen from a monocot haploid inducer plant or pollinating the monocot haploid inducer plant with pollen from a parent monocot target plant. Haploids are induced when egg or pollen carrying the cenh3 (i.e., null) allele, with diluted quantities of CENH3, are fertilized by pollen from a wild type line. Next, haploid progeny produced by the pollination are selected.

Methods of modifying the genome of a monocot target plant are also provided. The methods typically include inducing formation of a target haploid monocot plant expressing gene editing machinery, selecting haploid progeny with the genome of the monocot target plant but not the monocot haploid inducer plant, and wherein the genome of the haploid progeny has been modified by a site directed nuclease and optionally at least one guide RNA delivered by the monocot haploid inducer plant.

Any of the methods can further include additional steps, for example, chromosome doubling of the selected haploid progeny. Chromosome doubling can be spontaneous or induced by, for example, a chromosome doubling agent optionally selected from colchicine, pronamide, dithipyr, trifluralin, or another anti-microtubule agent.

The monocot haploid inducer plant can be, for example, maize, wheat, rice, sorghum, barley, oats, triticale, rye, pearl millet, finger millet, proso millet, foxtail millet, banana, bamboo, sugar cane, switchgrass, Miscanthus, asparagus, onion, garlic, chives, or yam. In a preferred embodiment, the haploid inducer plant is maize.

BRIEF DESCRIPTION OF THE DRAWINGS

FIG. 1A is a schematic showing construction of vectors for genome editing in maize. Ubi-Cas9 includes a codon-optimized Cas9 driven by the maize polyubiquitin promoter. gRNA-ImmuneCENIH13 includes a gRNA targeting the fourth exon of Cenh3 and an uncleavable mniuneCenH3 gene driven by 2.1 kb of the Cenh3 native promoter. Tailswap.CENH3 is based on ImmuneCEN/H3 but includes a modified N-terminal tail and a GFP tag. FIG. 1B is a schematic representation of the genomic structure of CENH3 gene. Exons are shown with boxes. The protospacer adjacent motif (PAM) and 20 bp target sequence of the sgRNA are also shown (SEQ ID NOS:16) aligned with complementary sequence/hybridizing segment of the sgRNA (SEQ ID NO:17). FIG. 1C is a chromatogram of the sequence from a heterozygous line showing the frameshift in the cenh3 null mutation (SEQ ID NOS:18-19). The PAM, the deletion, and the stop codon are illustrated.

FIGS. 2A and 2B are plots showing flow cytometric analysis of diploids and haploids. Diploid plants (2A) show peaks at 2N and 4N, where 4N is the result of endoreduplication in differentiated tissues. Haploid plants have 1N and 2N peaks (2B). FIGS. 2C and 2D are images of chromosome spreads. Maize diploids have 20 chromosomes (2C), whereas haploids have 10 (2D). FIGS. 2E and 2F are images of plants: haploids plants have a shorter stature (2E), and are sterile without exerted anthers (2F).

FIG. 3A shows aneuploids produced from gl8 crosses. Aneuploid_1 is trisomic for chromosome 3, and aneuploid_2 is monosomic for chromosome 2 and 4 and trisomic for chromosome 10. FIG. 3B shows aneuploids produced from gl1 crosses. Aneuploid_3 and aneuploid_4 are monosomic for chromosome 7, aneuploid_5 is monosomic for chromosome 3, 6 and 7, aneuploid_6 is monosomic for all the chromosomes except chromosome 1, and aneuploid_7 is monosomic for chromosome 9. The coverage in each sample was normalized to the coverage in the relevant diploid from each cross.

FIG. 5A is a plasmid map of the CRISPR construct used for simultaneous haploid induction and gene editing. Construct components are indicated. FIGS. 5B and 5C are photographs of wildtype (WT) (5B) and Young ear phenotype (fea2) (5C) phenotype (adapted from Taguchi-Shiobara, et al., *Genes Dev.* 15: 2755-2766 (2001), where the fea2 mutant phenotype was first described). FIG. 5D is a photograph of Young ear phenotype in the fea2 edited haploid plant obtained using the cenh3 haploid inducer.

DETAILED DESCRIPTION OF THE INVENTION

I. Definitions

Figure 1A:
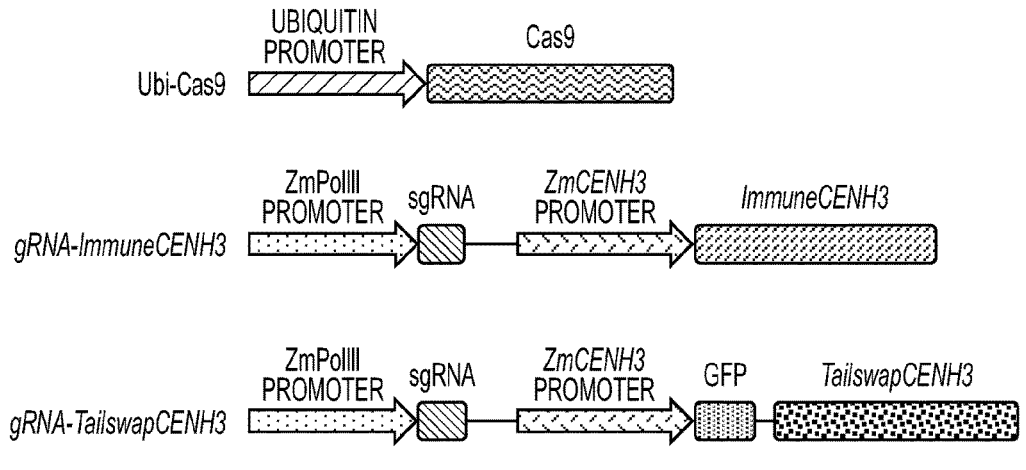
FIGS. 1A-1C illustrate the generation of the maize cenh3 null mutation by CRISPR/Cas9.

The term "about" is intended to describe values either above or below the stated value in a range of approx. +/−10%. The ranges are intended to be made clear by context, and no further limitation is implied. The use of any and all examples, or exemplary language (e.g., "such as") provided herein, is intended merely to better illuminate the description and does not pose a limitation on the scope of the description unless otherwise claimed.

The term "plant" is used in its broadest sense. It includes, but is not limited to, any species of woody, ornamental or decorative crop or cereal, and fruit or vegetable plant. It also refers to a plurality of plant cells that are largely differentiated into a structure that is present at any stage of a plant's development. Such structures include, but are not limited to, a fruit, shoot, stem, leaf, flower petal, etc.

The term "plant tissue" includes differentiated and undifferentiated tissues of plants including those present in roots, shoots, leaves, pollen, seeds and tumors, as well as cells in culture (e.g., single cells, protoplasts, embryos, callus, etc.). Plant tissue may be in planta, in organ culture, tissue culture, or cell culture. The term "plant part" as used herein refers to a plant structure, a plant organ, or a plant tissue.

The term "plant material" refers to leaves, stems, roots, flowers or flower parts, fruits, pollen, egg cells, zygotes, seeds, cuttings, cell or tissue cultures, or any other part or product of a plant.

The term "plant organ" refers to a distinct and visibly structured and differentiated part of a plant such as a root, stem, leaf, flower bud, or embryo.

The term "plant cell" refers to a structural and physiological unit of a plant, comprising a protoplast and a cell wall. The plant cell may be in form of an isolated single cell or a cultured cell, or as a part of higher organized unit such as, for example, a plant tissue, a plant organ, or a whole plant.

The term "plant cell culture" refers to cultures of plant units such as, for example, protoplasts, cell culture cells, cells in plant tissues, pollen, pollen tubes, ovules, embryo sacs, zygotes and embryos at various stages of development.

The term "transgenic plant" refers to a plant or tree that contains recombinant genetic material not normally found in plants or trees of this type and which has been introduced into the plant in question (or into progenitors of the plant) by human manipulation. Thus, a plant that is grown from a plant cell into which recombinant DNA is introduced by transformation is a transgenic plant, as are all offspring of that plant that contain the introduced transgene (whether produced sexually or asexually). It is understood that the term transgenic plant encompasses the entire plant or tree and parts of the plant or tree, for instance grains, seeds, flowers, leaves, roots, fruit, pollen, stems etc.

The term "construct" refers to a recombinant genetic molecule having one or more isolated polynucleotide sequences. Genetic constructs used for transgene expression in a host organism include in the 5'-3' direction, a promoter sequence; a sequence encoding a gene of interest; and a termination sequence. The construct may also include selectable marker gene(s) and other regulatory elements for expression.

The term "gene" refers to a DNA sequence that encodes through its template or messenger RNA a sequence of amino acids characteristic of a specific peptide, polypeptide, or protein. The term "gene" also refers to a DNA sequence that encodes an RNA product. The term gene as used herein with reference to genomic DNA includes intervening, non-coding regions as well as regulatory regions and can include 5' and 3' ends.

The term "orthologous genes" or "orthologs" refer to genes that have a similar nucleic acid sequence because they were separated by a speciation event.

The term, "polypeptide" refers generally to peptides and proteins having more than about ten amino acids. The polypeptides can be "exogenous," meaning that they are "heterologous," i.e., foreign to the host cell being utilized, such as human polypeptide produced by a bacterial cell.

The term "isolated" is meant to describe a compound of interest (e.g., nucleic acids) that is in an environment different from that in which the compound naturally occurs, e.g., separated from its natural milieu such as by concentrating a peptide to a concentration at which it is not found in nature. "Isolated" is meant to include compounds that are within samples that are substantially enriched for the compound of interest and/or in which the compound of interest is partially or substantially purified. Isolated nucleic acids are at least 60% free, preferably 75% free, and most preferably 90% free from other associated components. An "isolated" nucleic acid molecule or polynucleotide is a nucleic acid molecule that is identified and separated from at least one contaminant nucleic acid molecule with which it is ordinarily associated in the natural source. The isolated nucleic can be, for example, free of association with all components with which it is naturally associated. An isolated nucleic acid molecule is other than in the form or setting in which it is found in nature.

The term "locus" refers to a specific position along a chromosome or DNA sequence. Depending upon context, a locus could be a gene, a marker, a chromosomal band or a specific sequence of one or more nucleotides.

The term "allele" refers to one of two or more alternative forms of a gene.

The term "vector" refers to a replicon, such as a plasmid, phage, or cosmid, into which another DNA segment may be inserted so as to bring about the replication of the inserted segment. The vectors can be expression vectors.

The term "expression vector" refers to a vector that includes one or more expression control sequences.

The term "expression control sequence" refers to a DNA sequence that controls and regulates the transcription and/or translation of another DNA sequence. Control sequences that are suitable for prokaryotes, for example, include a promoter, optionally an operator sequence, a ribosome binding site, and the like. Eukaryotic cells are known to utilize promoters, polyadenylation signals, and enhancers.

The term "promoter" refers to a regulatory nucleic acid sequence, typically located upstream (5') of a gene or protein coding sequence that, in conjunction with various elements, is responsible for regulating the expression of the gene or protein coding sequence. The promoters suitable for use in the constructs of this disclosure are functional in plants and in host organisms used for expressing the disclosed polynucleotides. Many plant promoters are publicly known. These include constitutive promoters, inducible promoters, tissue- and cell-specific promoters and developmentally-regulated promoters. Exemplary promoters and fusion promoters are described, e.g., in U.S. Pat. No. 6,717,034, which is herein incorporated by reference in its entirety.

A nucleic acid sequence or polynucleotide is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading frame. Linking can be accomplished by ligation at convenient restriction sites. If such sites do not exist, synthetic oligonucleotide adaptors or linkers are used in accordance with conventional practice.

The terms "transformed," "transgenic," "transfected" and "recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed," "non-transgenic," or "non-recombinant" host refers to a wild-type organism, e.g., a bacterium or plant, which does not contain the heterologous nucleic acid molecule.

The term "endogenous" with regard to a nucleic acid refers to nucleic acids normally present in the host.

The term "heterologous" refers to elements occurring where they are not normally found. For example, a promoter may be linked to a heterologous nucleic acid sequence, e.g., a sequence that is not normally found operably linked to the promoter. When used herein to describe a promoter element, heterologous means a promoter element that differs from that normally found in the native promoter, either in sequence, species, or number. For example, a heterologous control element in a promoter sequence may be a control/regulatory element of a different promoter added to enhance promoter control, or an additional control element of the same promoter. The term "heterologous" thus can also encompasses "exogenous" and "non-native" elements.

As used herein, "homologous" means derived from the same species. For example, a homologous trait is any characteristic of organisms that is derived from a common ancestor. Homologous sequences can be orthologous or paralogous. Homologous sequences are orthologous if they were separated by a speciation event: when a species diverges into two separate species, the divergent copies of a single gene in the resulting species are said to be orthologous. Orthologs, or orthologous genes, are genes in different species that are similar to each other because they originated from a common ancestor. Homologous sequences are paralogous if they were separated by a gene duplication event: if a gene in an organism is duplicated to occupy two different positions in the same genome, then the two copies are paralogous.

As used herein, "polypeptide" refers generally to peptides and proteins having more than about ten amino acids. The polypeptides can be "exogenous," meaning that they are "heterologous," i.e., foreign to the host cell being utilized, such as human polypeptide produced by a bacterial cell.

As used herein, a "cultivar" refers to a cultivated variety.

As used herein, "germplasm" refers to one or more phenotypic characteristics, or one or more genes encoding said one or more phenotypic characteristics, capable of being transmitted between generations.

As used herein, the term "progenitor" refers to any of the species, varieties, cultivars, or germplasm, from which a plant is derived.

As used herein, the term "derivative species, germplasm or variety" refers to any plant species, germplasm or variety that is produced using a stated species, variety, cultivar, or germplasm, using standard procedures of sexual hybridization, recombinant DNA technology, tissue culture, mutagenesis, or a combination of any one or more said procedures.

As used herein, the terms "introgression", "introgressed" and "introgressing" refer to both a natural and artificial process whereby genes of one species, variety or cultivar are moved into the genome of another species, variety or cultivar, by crossing those species. The process may optionally be completed by backcrossing to the recurrent parent.

As used herein, "plant part" or "part of a plant" can include, but is not limited to cuttings, cells, protoplasts, cell tissue cultures, callus (calli), cell clumps, embryos, stamens, pollen, anthers, pistils, ovules, flowers, seed, petals, leaves, stems, and roots.

As used herein, a "hybrid" is typically derived from one or more crosses between different varieties, germplasms, populations, breeds or cultivars within a single species, between different subspecies within a species, or between different species within a genus. Typically, hybrids between subspecies are referred to as "intra-specific hybrids" and hybrids between different species within a genus are referred to as "interspecific hybrids."

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other forms the values may range in value either above or below the stated value in a range of approx. +/−5%; in other forms the values may range in value either above or below the stated value in a range of approx. +/−2%; in other forms the values may range in value either above or below the stated value in a range of approx. +/−1%. The preceding ranges are intended to be made clear by context, and no further limitation is implied.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a ligand is disclosed and discussed and a number of modifications that can be made to a number of molecules including the ligand are discussed, each and every combination and permutation of ligand and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. Further, each of the materials, compositions, components, etc. contemplated and disclosed as above can also be specifically and independently included or excluded from any group, subgroup, list, set, etc. of such materials.

These concepts apply to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

All methods described herein can be performed in any suitable order unless otherwise indicated or otherwise clearly contradicted by context. The use of any and all examples, or exemplary language (e.g., "such as") provided herein, is intended merely to better illuminate the embodiments and does not pose a limitation on the scope of the embodiments unless otherwise claimed. No language in the specification should be construed as indicating any non-claimed element as essential to the practice of the invention.

II. Plants

Haploid plants are widely used to accelerate the production of new inbred lines. Haploid induction involves a temporary diploid state followed by loss of one of the contributing genomes. This mechanism also makes it possible to introduce gene editing machinery in a genotype-independent manner without stably transforming the target line.

The disclosed methods utilize a simple null mutation of the Centromeric Histone H3 gene. Results presented in the Examples below show that heterozygous cenh3 null plant produces haploids at a frequency of 5% when crossed as a female and 0.5% when crossed as a male. The mechanism of haploid induction involves the sequential loss of chromosomes in the zygote. The disclosed plants and methods of use thereof also make it possible to introduce gene editing machinery to any line in a simple, rapid, and GMO-free way.

Maize gene nomenclature provides that mutant alleles are expressed in normal or italicized small font where the first letter is lowercase (e.g. cenh3), wild type genes are expressed in normal or italicized font where the first letter is uppercase (e.g. CenH3), and the expressed protein product is written with all letters in uppercase (CENH3). As the experiments described below were conducted in maize, maize nomenclature is generally followed herein. It will be appreciated, however, that the compositions and methods described herein are also applicable in, and thus also disclosed for, the corresponding gene in other monocot plants, thus use of this nomenclature should not be construed as limiting the disclosed compositions and methods to maize alone.

The disclosed haploid induction methods typically include a cross between a haploid inducer line, and a target line to be induced to generate haploids.

The disclosed gene editing methods typically include a cross between a haploid inducer line including gene editing machinery, and a target line to be induced to generate haploids which is also the target of gene modification. The in vivo haploid induction process is co-opted to introduce editing machinery into a target germplasm by including it in the haploid inducer parent. Typically the editing machinery is stably integrated as a transgene. Simultaneous editing plus haploid induction can be done in various monocots via wide cross or de novo haploid induction.

Typically, one or more of the plants utilized in the crosses disclosed herein, and/or the progeny generated therefrom, are non-naturally occurring plants. A "non-naturally occurring plant" refers to a plant that does not occur in nature without human intervention. Non-naturally occurring plants include transgenic plants as well as plants produced by non-transgenic means such as plant breeding.

A. Target Lines

The target line to be induced is typically a monocot. Monocots include one of the large divisions of Angiosperm plants (flowering plants with seeds protected within a vessel). They are herbaceous plants with parallel veined leaves and have an embryo with a single cotyledon, as opposed to dicot plants (dicotyledonous), which have an embryo with two cotyledons. In some embodiments, the target line is a monocot selected from maize, wheat, rice, sorghum, barley, oats, triticale, rye, pearl millet, finger millet, proso millet, foxtail millet, banana, bamboo, sugar cane, switchgrass, Miscanthus, asparagus, onion, garlic, chives, or yam.

The target line is typically one in which having a haploid plant, typically to accelerate production of new inbred lines, is desirable. In some embodiments, the target line is an elite inbred line where extensive breeding has already been performed, but genetic modifications are needed to improve the line so that, for example, it is resistant to disease or pest challenges or better adapted to different environments.

B. Inducer Lines

Haploid inducer plant lines optionally expressing gene editing machinery are provided. The inducer line is also a monocot, for example, maize, wheat, rice, sorghum, barley, oats, triticale, rye, pearl millet, finger millet, proso millet, foxtail millet, banana, bamboo, sugar cane, switchgrass, Miscanthus, asparagus, onion, garlic, chives, or yam.

The target and inducer lines can both be two plant lines that typically sexually reproduce. In other embodiments, the cross is an interspecific and intergeneric hybrid cross between related species or genera that do not normally sexually reproduce with each other. These crosses can also be referred to as wide crosses. In wheat, rice, barley, brassica, and other crops, the route to haploid induction can be to use a pollen donor that induces haploids via wide cross. For example, one could use corn pollen on wheat, millet pollen on wheat, barley pollen on other barley species, or any other wide crossing method.

As discussed in more detail below, the inducer plant is a heterozygous cenh3 null and optionally includes gene editing machinery.

1. cenh3 nulls

The inducer plants are heterozygous cenh3 nulls.

Exemplary GenBank accession number providing gene locations and sequences for CenH3 in various monocot plants include: maize, AF519807.2; rice, AY438639.1; wheat, JF969287.1; barley, JF419329.1; banana KP878235.1, each of which is incorporated by reference in its entirety, and which provide the following amino acid and nucleic acid (mRNA/cDNA) sequences for CENH3:

MARTKHQAVRKTAEKPKKKLQFERSGGASTSATPERAAGTGGRAASGGDSVKKTKPRHRWRPGTVALR

EIRKYQKSTEPLIPFAPFVRVVRELTNFVINGKVERYTAEALLALQEAAEFHLIELFEMANLCAIHAK

RVTIMQKDIQLARRIGGRRWA (SEQ ID NO: 20, maize, AF519807.2)

ctcccgtccc gagagttctg aatcgaaacc gtcggccacg agagcagtgc gaggcgccca ccgcgatggc tcgaaccaag caccaggccg tgaggaagac ggcggagaag cccaagaaga agctccagtt cgagcgctca ggtggtgcga gtacctcggc gacgccggaa agggctgctg ggaccggggg aagagcggcg tctggaggtg actcagttaa gaagacgaaa ccacgccacc gctggcggcc agggactgta gcgctgcggg agatcaggaa gtaccagaag tccactgaac cgctcatccc ctttgcgcct ttcgtccgtg tggtgaggga gttaaccaat ttcgtaacaa acgggaaagt agagcgctat accgcagaag ccctccttgc gctgcaagag gcagcagaat tccacttgat agaactgttt gaaatggcga atctgtgtgc catccatgcc aagcgtgtca caatcatgca aaaggacata caacttgcaa ggcgtatcgg aggaaggcgt tgggcatgat atataatatc cattctgatt gcatcattct tgtgaatttg tttgtaggag ctagacatta gtgttgttga atgctgcatg gttcctaatc cttttcgcag tctaacatct gtggagttag tatgttacat ggcaacagct gaacatctgt ggactataac tatatggcaa cagccgaaga ttgtgtctgt gggataactg gttgttttgg ttgctcttca gtagtttgtt tgcttcaggt aaccatgctg cgaactatga tgttttcatt ctcggtttgc ttcagctaac cgagatcgat tcagtctgca gtatatggac tatggagtaa actgcatgct gaaacccgaa ccactgctga aacggcagtt gccaggatag caggagggcc ctttatgcac agtggaattg agtagagaac tgagtaaacc atggttcttt ctccttttga actggaacac aaacacagtt ggatcttgtt tctcttctta ggccattgtc atcgtgtttc ttaggggtgt aaatggtatc tgtccgtatt cgaatttgat ctatctaaca aggctgaaat ccgaaaaaaa aaaaaaaaaa aaaaaaaaaa aaaaa (SEQ ID NO: 21, maize, AF519807.2)

MARTKHPAVRKSKAEPKKKLQFERSPRPSKAQRAGGGTGTSATTRSAAGTSASGTPRQQTKQRKPHRF

RPGTVALREIRKFQKTTELLIPFAPFSRLVREITDFYSKDVSRWTLEALLALQEAAEYHLVDIFEVSN

LCAIHAKRVTIMQKDMQLARRIGGRRPW (SEQ ID NO: 22, rice, AY438639.1)

acgccgcttc agtttgaaaa cccaccgcca cgtcgccgcc gccgccgccg ccgccgccga cgccgagatg gctcgcacga agcacccggc ggtgaggaag tcgaaggcgg agcccaagaa gaagctccag ttcgaacgct cccctcggcc gtcgaaggcg cagcgcgctg gtggcggcac gggtacctcg gcgaccacga ggagcgcggc tggaacatcg gcttcaggga cgcctaggca gcaaacgaag cagaggaagc cacaccgctt ccgtccaggc acagtggcac tgcgggagat caggaaattt cagaaaacca ccgaactgct gatcccgttt gcaccatttt ctcggctggt cagggagatc actgatttct attcaaagga tgtgtcacgg tggacccttg aagctctcct tgcattgcaa gaggcagcag aataccactt agtggacata tttgaagtgt caaatctctg cgccatccat gctaagcgtg ttaccatcat gcaaaaggac atgcaacttg ccaggcgtat cggtgggcgg aggccatggt gaaaatttgt ttgcgagcca tgcagcatga tggacaagga gcaacatgtg tcgttgatta acattttaga aagtagtgta gatgtatctt cacataggga tcaacttacc cttcgttccc attctaattc agttgatgtt agtatttacc ttttgctcca tttggattgg tcgaattcag gatttcatca aacagtcgat tgtgaaatgt gaaccaggaa ttgttgtgtt gattgcaata atgggttcct ctcaaaaaaa aaaaaaaa (SEQ ID NO: 23, rice, AY438639.1)

-continued

```
MARTKHPAVRKTKAPPKKQLGPRPAQRRQETDGAGTSATPRRAGRAAAPGGAQGATGQPKQRKPHRFR

PGTVALREIRRYQKSVDFLIPFAPFVRLIKEVTDFFCPEISRWTPQALVAIQEAAEYHLVDVFERANH

CAIHAKRVTVMQKDIQLARRIGGRRLW (SEQ ID NO: 24, wheat, JF969287.1)

atggcccgca ccaagcaccc ggccgtcagg aagaccaagg cgccgcccaa gaagcagctc gggccccgcc ccgcgcagcg gcggcaggag acagatggcg cgggcacgtc ggcgacaccg aggcgagccg ggcgggcggc ggccccaggg ggggctcaag gggcaactgg gcaacccaag cagaggaaac cacaccggtt caggccaggc acggtggcac tgcgggagat caggaggtat cagaagtcgg tcgactttct catcccgttt gcaccatttg tccgtctgat caaggaggtc accgacttct tctgtcctga aatcagccgc tggactcccc aagcgctcgt cgcgattcaa gaggctgcag agtatcacct cgtcgacgta tttgaaaggg caaatcactg tgccatccat gcaaagcgtg ttaccgtcat gcaaaaggac atacagcttg caaggcgtat cggcgggagg aggctttggt ga (SEQ ID NO: 25, wheat, JF969287.1)

MARTKKTVAAKEKRPPCSKSEPQSQPKKKEKRAYRFRPGTVALREIRKYRKSTNMLIPFAPFVRLVRD

IADNLTPLSNKKESKPTPWTPLALLSLQESAEYHLVDLFGKANLCAIHSHRVTIMLKDMQLARRIGTR

SLW (SEQ ID NO: 26, barley, JF419329.1)

gaacgaactc tatctctctc tctgcctgct ttccccacct gcgatggctc gcacgaagaa aacggtggcg gcgaaggaga agcgcccccc ttgctccaag tcggagccgc agtcgcagcc gaagaagaag gagaagcggg cgtaccggtt ccggccgggc acggtggcgc tgcgggagat ccggaagtac cgcaagtcca ccaatatgct catccccttt gcgcccttcg tccgcctggt cagggacatc gccgacaact tgacgccatt gtcgaacaag aaggagagca agccgacgcc atggactcct ctcgcgctcc tctcgttgca agagtctgca gagtatcact tggtcgatct atttggaaag gcaaatctgt gtgccattca ttcgcaccgt gttaccatca tgctaaagga catgcagctt gcgaggcgta tcgggacgag aagcctttgg tgatactaat ggaggatgtt ttaggcatcg tagggagcaa acactggtga tgctaatggt agatgttttt tgtatgagtg caatgcgaag gagctgatgg tagtgatcca atatgtttgt gagtgtatca ttaggaagta atgtaggtgt gttttcatct aggtagcatg tcttcgaagt tgatccggtt ggttgcatgg ctgggatcat ctgacttgtc ggcttttgct ccatttgaat tgatctaatt cggacagagt ttctgcaaat gatccaataa tatgggttgc caaaaaaaaa aaaaaaat
(SEQ ID NO: 27, barley, JF419329.1)

MARTKHLSNRSSSRPRKRFHFGRSPGQRTPADANRPATPSGATPRTTATRSRDTPQGAPSQSKQQPRR

RRFRPGVVALREIRNLQKTWNLLIPFAPFVRLVREITHFYSKEVNRWTPEALVAIQEAAETHMIEMFE

DAYLCAIHAKRVTLMQKDIHLARRIGGRRHW (SEQ ID NO: 28, banana, KP878235.1)

atggcgagaa cgaagcatct gtccaacagg tcctcctctc gccctcggaa gcgcttccat ttcggtcggt ctccagggca gcgaacccccc gctgatgcga tcggcctgc gacgccatct ggtgctacte ctagaaccac ggccaccaga tcgagggata cgcctcaagg ggcaccgagc caatcaaaac agcagccgag gcggcgcagg tttaggccgg gggtggtggc gctacgcgag atcaggaatt gcagaagac gtggaatcta ttgatccctt tcgctccgtt tgtcagactt gttcgggaga tcactcattt ctactcgaaa gaagtaaacc gatggacccc tgaagcttta gttgcgattc aagaggcagc ggaaactcat atgatagaaa tgtttgaaga tgcatatctc
```

-continued
tgtgcaattc atgcaaaacg tgttaccctt atgcaaaaag atatccatct agcaaggcga ataggaggaa gaagacattg gtga (SEQ ID NO: 29, banana, KP878235.1)

The Cenh3 gene is conserved across all plants, fungi, and animals, with few exceptions in some insect lineages. It serves the fundamentally important role of defining the boundaries of the functional centromere, and initiating and organizing the kinetochore (Cheeseman and Desai, *Nature Reviews Molecular Cell Biology,* 9:33-46 (2008). The CENH3 wildtype can be the CENH3 of the monocot inducer plant, e.g., maize, wheat, rice, sorghum, barley, oats, triticale, rye, pearl millet, finger millet, proso millet, foxtail millet, banana, bamboo, sugar cane, switchgrass, Miscanthus, asparagus, onion, garlic, chives, or yam. In some embodiments, the wildtype CENH3 has the amino acid sequence of any one of SEQ ID NOS:20, 22, 24, 26, or 28, or an amino acid sequence having at least 75%, 80%, 85%, 90%, 95% or more sequence identity thereto; is encoded by the nucleic acid of any one of SEQ ID NOS:21, 23, 25, 27, or 29, a nucleic acid having at least 75%, 80%, 85%, 90%, 95%, more sequence identity thereto; is a homologue such as an orthologue or paralogue of the foregoing sequences; or any combination thereof.

A null allele is a nonfunctional allele caused by a genetic mutation. Such mutations can cause a complete lack of production of the associated gene product or a product that does not function properly; in either case, the allele is considered nonfunctional. For example, CENH3 protein binds to DNA and recruits all overlying proteins that form the kinetochore that mediates chromosome segregation in a plant cell. Non-functional CENH3 will not contribute to the formation of a centromere, kinetochore formation, and/or chromosome segregation in a plant cell. A null, which encodes no functional protein, is distinguished from CENH3 variants such as GFP-tailswap or variants that produce altered or partially deleted CENH3 proteins. See, e.g., Kuppu, et al., "A Variety of Changes, Including CRISPR/Cas9-mediated Deletions, in CENH3 Lead to Haploid Induction on Outcrossing", *Plant Biotechnol J,* 2020, doi: 10.1111/pbi.13365, which is specifically incorporated by references herein in its entirety. GFP-tailswap and variant forms can substitute for native CENH3 and retain sufficient function to organize kinetochores, even if imperfectly. Null alleles are a special category of mutation that cause a total loss of function.

Figure 1B:
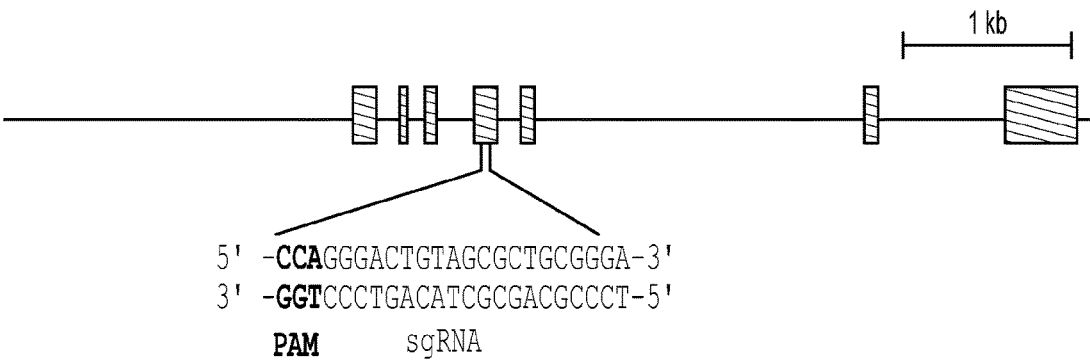
Figure 1C:
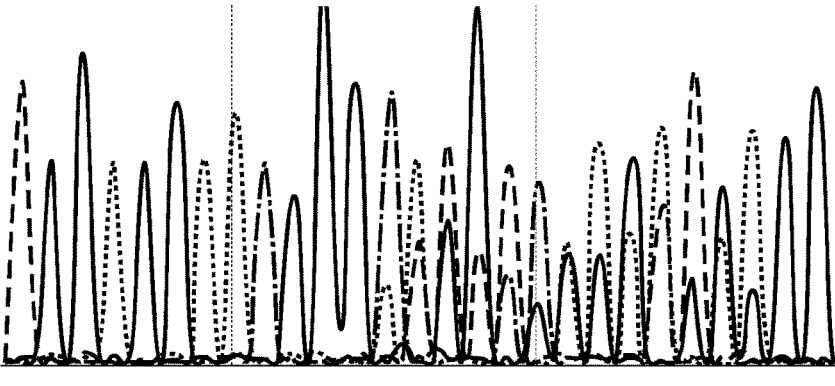

A mutant allele that produces no RNA transcript is called an RNA null (shown by Northern blotting, total RNA sequencing, or by DNA sequencing of a deletion allele), and one that produces no protein is called a protein null (shown by Western blotting). Nulls are frequently caused by frameshift mutations. The genetic code is read in triplets of nucleotides, such that any sequence can be read in three frames, where only one is correct. Mutations that cause a small deletion or addition of nucleotides can shift the reading frame to a nonsensical protein and often cause protein translation to stop prematurely. Frameshift mutations that cause a premature stop, particularly when most of the predicted protein is absent, are generally interpreted as null alleles. For example, a frameshift mutation that causes a stop codon in the N-terminal tail of CENH3 encodes a severely truncated protein that lacks the capacity to bind to DNA or other histones (FIG. 1C). A genetic null or amorphic allele has the same phenotype when homozygous as when heterozygous with a deficiency that disrupts the locus in question. A genetic null allele may be both a protein null and an RNA null, but may also express normal levels of a gene product that is nonfunctional due to mutation. The cenh3 null allele can be a deletion of the entire locus or mutation of one or more nucleotides therein leading to lack of production of cenh3 gene product or a product that does not function properly. The cenh3 null allele can be an RNA null, a protein null, or both.

The null allele of the disclosed cenh3 nulls is typically distinguishable from GFP-tailswap constructs and several variants of Cenh3 such as those described in U.S. Pat. No. 8,618,354, U.S. Published Application No. 2018/0116141, U.S. Published Application No. 2019/0343060, and WO 2017/004375, which create CENH3 variant proteins that are functional, albeit reduced or altered in function or level relative to a wildtype cenh3 allele.

In some embodiments, a sperm carrying the cenh3 null has no more than 25% of the normal amount of a functional (e.g., wildtype) CENH3 protein and an egg carrying the cenh3 null has more than 12.5% of a functional (e.g., wildtype) CENH3 protein.

In some embodiments, the heterozygous cenh3 null inducer line does not include a recombinant gene expressing mutant or variant CENH3. Thus, in some embodiments, the null is not complemented by non-endogenous CENH3 expression. In some embodiments, quantitative reductions in CENH3 alone induce centromere-mediated haploid induction.

In some embodiments, the only functional CENH3 in the heterozygous cenh3 null inducer line is expressed from the endogenous wildtype allele of the heterozygous cenh3 null.

A non-limiting method for making a cenh3 null is described below. Briefly, a transgenic line containing Cas9 was crossed to another transgenic line containing a guide RNA targeting the first exon of CenH3 as well as an intact full-length genomic clone of CenH3 that contains five silent nucleotide changes over guide RNA site (FIGS. 1A-1C; the uncleavable gene is referred to as ImmuneCenH3). When lines containing these constructs were crossed together, Cas9 mutated native cenh3 while CenH3 function was covered by the ImmuneCenH3 gene. Thus, in some embodiments, the null allele has one or more mutation(s) in the first exon that abolishes expression of functional protein from the null allele. In some embodiments, the null is caused by a mutation in the sequence encoding the N-terminal tail that removes all CENH3 protein sequence that interacts with DNA or other histories.

Figure 4A:
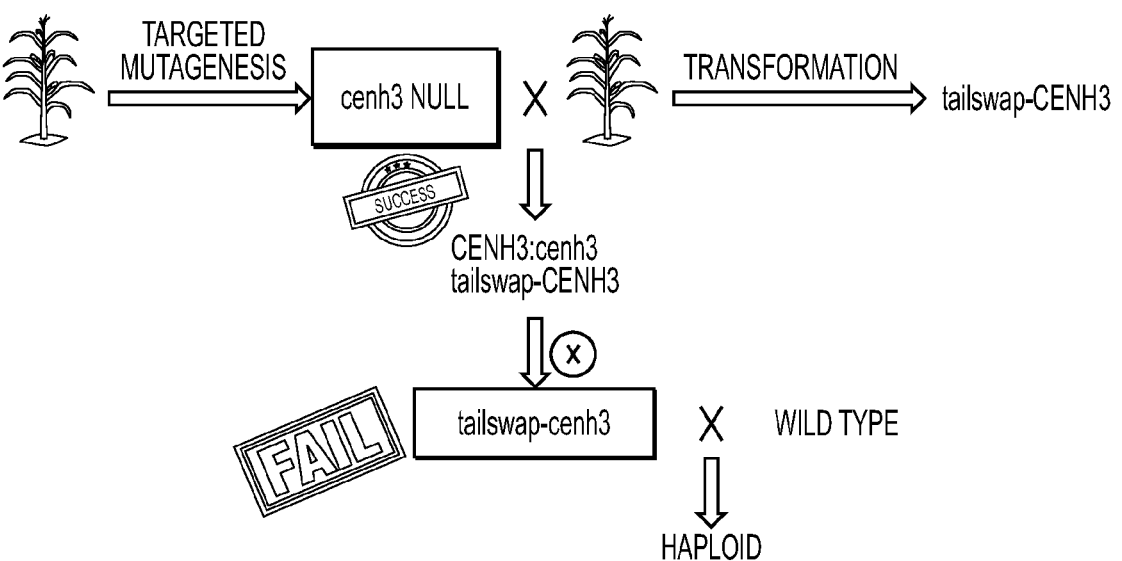
FIG. 4A is a flow diagram showing a failed strategy for creating a Tailswap-CENH3 inducer line in maize. ImmuneCenH3 was swapped with a maize version of the GFP-tailswap construct and several other variants of Cenh3 to see if the lines would induce haploids. None of these CenH3 variants complemented the null ("fail").
Figure 4B:
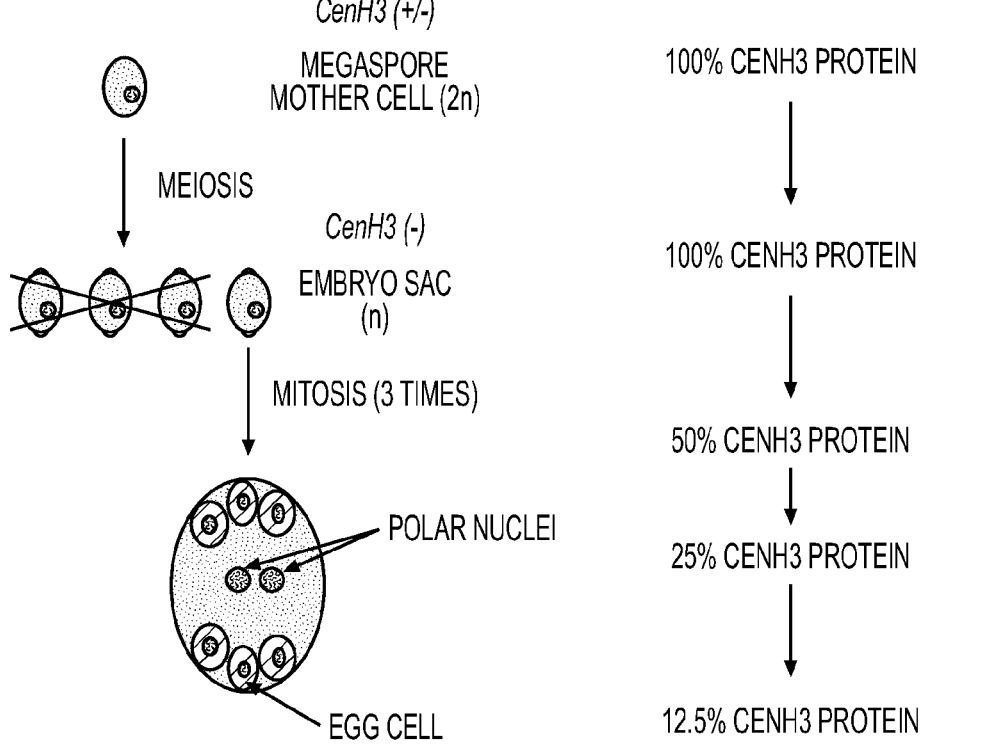
FIG. 4B is flow diagram showing the distribution of CENH3 during female gamete development. In the female gametophyte there are three cell divisions that precede the formation of an egg. An egg carrying the cenh3 null can have no more than 12.5% CENH3 protein.

At each cell division, CENH3 is naturally divided equally between the replicated DNA strands at S phase and replenished later in G2 (Lermontova et al., *The Plant Journal: For Cell and Molecular Biology,* 68 (1): 40-50 (2006)). This cannot occur in a haploid cell that is null for cenh3, and the cell cycle must proceed with half as much CENH3 than would normally be present. In the male gametophyte (pollen), there are two cell divisions the precede the formation of sperm, and in female gametophyte there are three cell divisions that precede the formation of an egg. A sperm carrying the cenh3 null can have no more than 25% of the normal amount of CENH3 and an egg carrying the cenh3 null can have no more than 12.5% (FIG. 4B). The results also show that 0.5% of the progeny from the male carrying the cenh3 null are haploid, and 5.0% of the progeny from the female are haploid. Thus, the inducer can be used as either the male or as the female of the cross. Female inducers generate a higher percentage of haploids, thus, in some embodiments, the haploid inducer is preferably a female, but alternatively, the methods can be conducted using the haploid inducer as the male.

2. Markers

The haploid inducer can have a marker that can assist in identifying seeds that are haploid. For example, the haploid inducer can have a dominant purple pigment gene (e.g., R1-nj). The seeds of haploid individuals have a purple aleurone, but lack purple pigment in the endosperm (scutellum), indicating that the germline does not contain the haploid inducer chromosomes. Seeds that have a yellow endosperm and a purple aleurone are planted out and grown up to be seedlings. These seedlings have their chromosome number doubled using colchicine or other methods as discussed in more detail below. The chromosome doubled haploids are grown in a greenhouse and or transplanted to the field, and the chromosome doubled plants are self-pollinated to produce doubled haploid seed as discussed in more detail elsewhere herein.

3. Gene Editing Machinery

The inducer line also optionally includes gene editing machinery. For example, the inducer plant can have encoded into its DNA the machinery necessary for accomplishing the editing in the target plant's genome.

Targeted mutagenesis (also known as gene editing) is a very important technology to crop breeding. There are numerous methods to edit specific gene targets now, including CRISPR, TALEN, meganucleases, and zinc fingers. The endonuclease can be designed to target nearly any sequence. The endonuclease(s) can be constructed using methods such as, but not limited to, those described by Svitashev, et al., *Plant Physiology*, 169: 931-945 (2015), Lee, et al., *Plant Biotechnology*, 17(2):362-372 (2019)), Sander et al., *Nature Met*, 8(1):67-69, (2011), Cermak et al., *Nucl Acids Res*, 39(17):7879 (2011); with correction at *Nucl Acids Res*, 39:e82. doi: 10.1093/nar/gkr218, 2011), and Liang et al., et al., *J Genet Genom*, 41(2):63-68, (2014). The promoter used to drive expression of the endonuclease can be one expressed throughout development or specifically in egg cells or during early embryo development, and can be endogenous or exogenous. Examples of promoters 35S (CaMV d35S) or derivatives (e.g., double 35S) ZmUb1 (maize) APX (rice) OsCc1 (rice) EIF5 (rice) R1G1B (rice) PGD1 (rice) Act1 (rice) SCP1 (rice).

The gene editing machinery construct(s) may include a selectable marker (e.g., herbicide resistance) to assist with recovery of the transgene during whole plant transformation and subsequent backcrossing. In some cases, one or more (e.g., two or more, or three or more) endonucleases and/or CRISPR guide RNAs are combined into a single construct to target one or sequences of DNA.

One method to introduce editing machinery into plants is to use an Agrobacterium-based method (such as the method described by Ishida et al., *Nature Biotechnol*, 146:745-750 (1996)) or particle bombardment (such as the method described by Gordon-Kamm et al., *Plant Cell Online*, 2(7): 603-618 (1990)) on plant tissue. Newer methods that incorporate developmental regulator genes have been devised that make it possible to transform plants without extensive tissue culture. See, e.g., Lowe, et al., *The Plant Cell*, 28: 1998-2015 (2016). In transformation, DNA coding for the editing machinery (e.g., CAS9 and guide RNA) is introduced into plant callus, seed or embryonic tissue. Stably-transformed plants (events) are then recovered, optionally with the help of a selectable marker.

Alternatively, a line amenable to transformation is first transformed with the gene editing machinery, and the resulting line is then crossed to a haploid inducer line. The resulting $F_1$ that is heterozygous for cenh3 itself becomes a haploid inducer. No additional backcrossing is needed. In this case, the $F_1$ haploid inducer line contains the endonuclease transgene. Next, the inducer line carrying (e.g., encoding, expressing, etc.) the gene editing machinery can be pollinated by a second plant to be edited. From that pollination event, progeny (e.g., embryos or seeds) are produced; at least one of which will be a haploid seed. This haploid seed will only contain the chromosomes of the second plant; the inducer plant's chromosomes have vanished (having been eliminated, lost or degraded), but before doing so, the inducer plant's chromosomes permitted the gene-editing machinery to be expressed.

Alternately, and without wishing to be bound by theory, the inducer plant delivers the already-expressed editing machinery upon pollination via the pollen tube. Or, in the case that the haploid inducer line is the female in the cross, the haploid inducing plant's egg cell contains the editing machinery that is present and perhaps already being expressed, upon fertilization with the "wild type" or non-haploid inducing pollen grain. Through any of these routes, the haploid progeny obtained by the cross will also have had its genome edited. In the case of maize, where many crosses can be made with a single male plant, the $F_1$ containing the cenh3 null and gene editing machinery can be used to edit multiple lines by making multiple separate crosses.

The gene editing machinery typically includes an element or elements that induce a single or a double strand break in the target cell's genome. For example, the editing machinery can be any DNA modification enzyme, but is preferably a site-directed nuclease. The site-directed nuclease is preferably CRISPR-based, but could also be a meganuclease, a transcription-activator like effector nuclease (TALEN), or a zinc finger nuclease. The nuclease, for example, can be Cas9 or Cfp1/Cas12a. In one aspect, the nuclease is designed to cleave the DNA, with the intent of creating small deletions or duplications at the target site. The resulting small deletions and duplication can knock out gene function.

In another aspect, the DNA modification enzyme is a site-directed base editing enzyme such as Cas9-cytidine deaminase or Cas9-adenine deaminase, wherein the Cas9 can have one or both of its nuclease activities inactivated, i.e. dCas9.

In yet another embodiment, the gene editing machinery can be combined with an additional repair template, such that cleavage is followed by homology-directed repair (HDR), resulting in the modification or replacement of DNA at the target site. The purpose of the haploid inducer in this context is as a means to rapidly transfer the gene editing machinery from a transformable line into any other line without passing through a tissue culture phase or repeated backcrossing.

Gene editing machinery that can be used are discussed in more detail below.

a. Strand Break Inducing Elements i. CRISPR/Cas

In preferred embodiments, the element that induces a single or a double strand break in the target cell's genome is a CRISPR/Cas system. As in other animal model systems, Cas9 and sgRNA expression within targeted cells is sufficient to modify plant genomes (Deepa, et al., *Front. Plant Sci.*, 9:985 (2018), doi:10.3389/fpls.2018.00985. While Cas9 is commonly used, any CRISPR/Cas-based system, for instance Cfp1/Cas12a can be used in a similar manner (Tang, et al., *Genome Biology,* 19(84) (2018), doi/10.1186/s13059-018-1458-5). Broadly useful RNA polymerase II promoters (such as 35S or ZmUb1) are often used to express Cas genes, but promoters expressing in egg cells may be more applicable in the current application. Plant-specific RNA polymerase III promoters [AtU6 (Arabidopsis); TaU6 (wheat); OsU6 or OsU3 (rice)]have been used to express sgRNA in plant systems. Other embodiments may involve multiplexed guide RNA systems driven by other promoters (Lowder, et al., *Plant Physiol.,* 169(2): 971-985 (2015), He, et al., J Genet Genomics, 20; 44(9): 469-472 (2017)). The Cas genes may be fully functional and designed to create double stranded breaks that are repaired by non-homologous end joining (NHEJ), resulting in mutations that knock out gene function. Alternatively Cas genes may be partially inactivated so as to cause single stranded nicks (e.g. nCas9), or fully inactivated (e.g. dCas9) to bind and not cleave, but simply direct another enzyme such as an adenine or cytidine deaminase to the desired site (Eid, et al., *Biochem J,* 475 (11): 1955-1964 (2018)). There are several commercially available vectors for expressing Cas9 or Cas9 variants and gRNAs in plant systems, and include empty gRNA backbones having a plant RNA polymerase III promoter and gRNA scaffolds to which a practitioner can insert the gRNA of interest. CRISPR-based systems can also be adapted to alter genes by homology directed repair, as described below. One constraint is that CRISPR applications utilize sequences that include short Protospacer Adjacent Motifs (PAM sites).

The inducer plant's genome can include one or more nucleic acids encoding a Cas enzyme and a guide RNA as components of a CRISPR system. The inducer plant's genome can optionally include a donor polynucleotide sequence to be recombined into the target cell's genome at or adjacent to the target site (e.g., the site of single or double stand break induced by the Cas9).

Methods of preparing compositions for use in genome editing using the CRISPR/Cas systems are described in detail in, for example, WO 2013/176772, WO 2014/018423, Cong, *Science,* 15:339(6121):819-823 (2013), and Jinek, et al., *Science,* 337(6096):816-21 (2012).

In general, "CRISPR system" refers collectively to transcripts and other elements involved in the expression of or directing the activity of CRISPR-associated ("Cas") genes, including a Cas protein or sequences encoding a Cas gene, a tracr (trans-activating CRISPR) sequence (e.g., tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or other sequences and transcripts from a CRISPR locus. One or more tracr mate sequences operably linked to a guide sequence (e.g., direct repeat-spacer-direct repeat) can also be referred to as pre-crRNA (pre-CRISPR RNA) before processing or crRNA after processing by a nuclease.

In some embodiments, a tracrRNA and crRNA are linked and form a chimeric crRNA-tracrRNA hybrid where a mature crRNA is fused to a partial tracrRNA via a synthetic stem loop to mimic the natural crRNA:tracrRNA duplex as described in Cong, *Science,* 15:339(6121):819-823 (2013) and Jinek, et al., *Science,* 337(6096):816-21 (2012)). A single fused crRNA-tracrRNA construct is also referred to herein as a guide RNA or gRNA (or single-guide RNA (sgRNA)). Within a sgRNA, the crRNA portion can be identified as the 'target sequence' and the tracrRNA is often referred to as the 'scaffold'.

In some embodiments, one or more elements of a CRISPR system is derived from a type I, type II, or type III CRISPR system. In some embodiments, one or more elements of a CRISPR system is derived from a particular organism including an endogenous CRISPR system, such as *Streptococcus pyogenes.*

In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. A target sequence can be any polynucleotide, such as DNA or RNA polynucleotides. In some embodiments, a target sequence is located in the nucleus or cytoplasm of a cell.

In the target nucleic acid, each protospacer is associated with a protospacer adjacent motif (PAM) whose recognition is specific to individual CRISPR systems. In the *Streptococcus pyogenes* CRISPR/Cas system, the PAM is the nucleotide sequence NGG. In the *Streptococcus* thermophiles CRISPR/Cas system, the PAM is the nucleotide sequence is NNAGAAW. The tracrRNA duplex directs Cas to the DNA target consisting of the protospacer and the requisite PAM via heteroduplex formation between the spacer region of the crRNA and the protospacer DNA.

There are many resources available for helping practitioners determine suitable target sites once a desired DNA target sequence is identified. See e.g., crispr.u-psud.fr/, a tool designed to help scientists find CRISPR targeting sites in a wide range of species and generate the appropriate crRNA sequence.

In some embodiments, one or more polynucleotides driving expression of one or more elements of a CRISPR system are introduced into the inducer plant's genome such that expression of the elements of the CRISPR system direct formation of a CRISPR complex at one or more target sites. For example, a Cas enzyme, and one or more a guide sequence linked to a tracr-mate sequence, and a tracr sequence could each be operably linked to separate regulatory elements on separate expression constructs (e.g., sgRNAs). Alternatively, two or more of the elements expressed from the same or different regulatory elements may be combined in a single construct, with one or more additional constructs providing any components of the CRISPR system not included in the first construct. CRISPR system elements that are combined in a single construct may be arranged in any suitable orientation, such as one element located 5' with respect to ("upstream" of) or 3' with respect to ("downstream" of) a second element. The coding sequence of one element can be located on the same or opposite strand of the coding sequence of a second element, and oriented in the same or opposite direction. In some embodiments, a single promoter drives expression of a transcript encoding a CRISPR enzyme and one or more of the guide sequence, tracr mate sequence (optionally operably linked to the guide sequence), and a tracr sequence embedded within one or more intron sequences (e.g., each in a different intron, two or more in at least one intron, or all in a single intron).

In some embodiments, the CRISPR enzyme, guide sequence, tracr mate sequence, and tracr sequence are operably linked to and expressed from the same promoter.

In some embodiments, a construct includes a regulatory element operably linked to an enzyme-coding sequence encoding a CRISPR enzyme, such as a Cas protein.

Non-limiting examples of Cas proteins include Casl, CaslB, Cas2, Cas3, Cas4, Cas5, Cas6, Cas7, Cas8, Cas9 (also known as Csnl and Csxl2), CaslO, Csyl, Csy2, Csy3, Csel, Cse2, Cscl, Csc2, Csa5, Csn2, Csm2, Csm3, Csm4, Csm5, Csm6, Cmrl, Cmr3, Cmr4, Cmr5, Cmr6, Csbl, Csb2, Csb3, Csxl7, Csxl4, CsxlO, Csxl6, CsaX, Csx3, Csxl, Csxl5, Csfl, Csf2, Csf3, Csf4, homologues thereof, or modified versions thereof. In some embodiments, the unmodified CRISPR enzyme has DNA cleavage activity, such as Cas9. In some embodiments, the CRISPR enzyme directs cleavage of one or both strands at the location of a target sequence, such as within the target sequence and/or within the complement of the target sequence.

In some embodiments, a construct encodes a CRISPR enzyme that is mutated with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). Other examples of mutations that render Cas9 a nickase include, without limitation, H840A, N854A, and N863A. As a further example, two or more catalytic domains of Cas9 (RuvC I, RuvC II, and RuvC III) can be mutated to produce a mutated Cas9 substantially lacking all DNA cleavage activity. In some embodiments, a D10A mutation is combined with one or more of H840A, N854A, or N863A mutations to produce a Cas9 enzyme substantially lacking all DNA cleavage activity. In some embodiments, a CRISPR enzyme is considered to substantially lack all DNA cleavage activity when the DNA cleavage activity of the mutated enzyme is less than about 25%, 10%, 5%>, 1%>, 0.1%>, 0.01%, or lower with respect to its non-mutated form.

In some embodiments, an enzyme coding sequence encoding a CRISPR enzyme is codon optimized for expression in particular cells. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules.

The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database", and these tables can be adapted in a number of ways. See Nakamura, Y., et al., *Nucl. Acids Res.,* 28:292 (2000). Computer algorithms for codon optimizing a particular sequence for expression in a particular host cell, for example Gene Forge (Aptagen; Jacobus, PA), are also available. In some embodiments, one or more codons (e.g., 1, 2, 3, 4, 5, 10, 15, 20, 25, 50, or more, or all codons) in a sequence encoding a CRISPR enzyme correspond to the most frequently used codon for a particular amino acid.

While the specifics can be varied in different engineered CRISPR systems, the overall methodology is similar. A practitioner interested in using CRISPR technology to target a DNA sequence (identified using one of the many available online tools) can insert a short DNA fragment containing the target sequence into a guide RNA expression construct. The sgRNA expression construct contains the target sequence (about 20 nucleotides), a form of the tracrRNA sequence (the scaffold) as well as a suitable promoter and necessary elements for proper processing in target cells. In some embodiments, multiple guide RNAs are expressed from one construct, either by chaining together multiple expression cassettes with RNA Polymerase III promoters, or by engineering long RNAs that include tRNAs or ribozyme self-cleavage sites that liberate multiple functional sgRNAs, either targeting one or several genes (Cermak, et al., *Plant Cell,* 29(6): 1196-1217 (2017), He, et al., *J Genet Genomics,* 44(9): 469-472 (2017)). Vectors are commercially available (see, for example, Addgene). Many of the systems rely on custom, complementary oligos that are annealed to form a double stranded DNA and then cloned into the sgRNA expression plasmid. Co-expression of the sgRNAs and the appropriate Cas enzyme from the same or separate constructs in cells results in a single or double strand break (depending of the activity of the Cas enzyme) at the desired target site. CRISPR/Cas gene editing approaches are fully compatible with the cenh3 haploid inducer system, and the two technologies can be usefully combined to facilitate genotype-independent gene editing.

ii. Zinc Finger Nucleases

In some embodiments, the element that induces a single or a double strand break in the target plant's genome is a nucleic acid construct or constructs encoding a zinc finger nucleases (ZFNs). ZFNs are typically fusion proteins that include a DNA-binding domain derived from a zinc-finger protein linked to a cleavage domain such as the Type IIS enzyme Fok I (Miller, et al., *Nature Biotechnology,* 25:778-785(2007)). Fok I catalyzes double-stranded cleavage of DNA at 9 nucleotides from its recognition site on one strand and 13 nucleotides from its recognition site on the other. See, also, U.S. Pat. Nos. 5,356,802; 5,436,150 and 5,487,994; as well as Li et al. *Proc., Natl. Acad. Sci. USA* 89 (1992):4275-4279; Li et al. *Proc. Natl. Acad. Sci. USA,* 90:2764-2768 (1993); Kim et al. *Proc. Natl. Acad. Sci. USA.* 91:883-887 (1994a); Kim et al. *J. Biol. Chem.* 269:31,978-31,982 (1994b). One or more of these enzymes (or enzymatically functional fragments thereof) can be used as a source of cleavage domains.

Exemplary Type IIS restriction enzymes are described in International Publication WO 07/014275. Additional restriction enzymes also contain separable binding and cleavage domains. See, for example, Roberts et al. *Nucleic Acids Res.,* 31:418-420 (2003). In certain embodiments, the cleavage domain includes one or more engineered cleavage half-domain (also referred to as dimerization domain mutants) that minimize or prevent homodimerization, as described, for example, in U.S. Published Application Nos. 2005/0064474, 2006/0188987, and 2008/0131962. In certain embodiments the cleavage half domain is a mutant of the wild type Fok I cleavage half domain. In some embodiments the cleavage half domains are modified to include nuclear or other localization signals, peptide tags, or other binding domains.

The DNA-binding domain, which can, in principle, be designed to target any genomic location of interest, can be a tandem array of $Cys_2His_2$ zinc fingers, each of which generally recognizes three to four nucleotides in the target DNA sequence. By linking together multiple fingers (the number varies: three to six fingers have been used per monomer in published studies), ZFN pairs can be designed to bind to genomic sequences 18-36 nucleotides long.

Another type of zinc finger, called a $Cys_2Cys_2$ zinc finger, binds zinc between 2 pairs of cysteines has been found in a range of DNA binding proteins.

The DNA-binding domain of a ZFN can be composed of two to six zinc fingers. Each zinc finger motif is typically considered to recognize and bind to a three-base pair sequence and as such, a protein including more zinc fingers targets a longer sequence and therefore may have a greater specificity and affinity to the target site. Zinc finger binding domains can be "engineered" to bind to a predetermined nucleotide sequence. See, for example, Beerli et al. *Nature Biotechnol.* 20: 135-141 (2002); Pabo et al. *Ann. Rev. Biochem.* 70:313-340 (2001); Isalan et al., *Nature Biotechnol.* 19:656-660 (2001); Segal et al. *Curr. Opin. Biotechnol.* 12:632-637 (2001); Choo et al., *Curr. Opin. Struct. Biol.* 10:41 1-416 (2000).

Standard ZFNs fuse the cleavage domain to the C-terminus of each zinc finger domain. In order to allow the two cleavage domains to dimerize and cleave DNA, the two individual ZFNs must bind opposite strands of DNA with their C-termini a certain distance apart, generally 5 to 7 bp. Both single-stranded cleavage and double-stranded cleavage are possible, and double-stranded cleavage can occur as a result of two distinct single-stranded cleavage events. Repair of zinc finger-induced double stranded breaks generally occurs by non-homologous end joining (NHEJ) and results in mutations that knock out gene function. Zinc finger nuclease systems can also be combined with a second construct containing donor molecule to insert new DNA sequences by homology-directed repair as described below.

See also Shukla, et al., *Nature*, 459, 437-441(2009). See, also, U.S. Pat. Nos. 6,140,081; 6,453,242; 6,534,261; 6,610, 512; 6,746,838; 6,866,997; 7,067,617; U.S. Published Application Nos. 2002/0165356; 2004/0197892; 2007/0154989; 2007/0213269; and International Patent Application Publication Nos. WO 98/53059 and WO 2003/016496, for further design considerations.

A strength of the zinc-finger nucleases is that any site can be targeted, and it is not limited by the PAM sites that are needed for Cas9 targeting. Zinc finger nuclease approaches are fully compatible with the cenh3 haploid inducer system, and the two technologies can be usefully combined to facilitate genotype-independent gene editing.

iii. Transcription Activator-Like Effector Nucleases

In some embodiments, the element that induces a single or a double strand break in the target plant's genome is a nucleic acid construct or constructs encoding a transcription activator-like effector nuclease (TALEN). TALENs have an overall architecture similar to that of ZFNs, with the main difference that the DNA-binding domain comes from TAL effector proteins, transcription factors from plant pathogenic bacteria. The DNA-binding domain of a TALEN is a tandem array of amino acid repeats, each about 34 residues long. The repeats are very similar to each other; typically they differ principally at two positions (amino acids 12 and 13, called the repeat variable diresidue, or RVD). Each RVD specifies preferential binding to one of the four possible nucleotides, meaning that each TALEN repeat binds to a single base pair, though the NN RVD is known to bind adenines in addition to guanine. Like zinc finger systems, RVDs are linked together to confer specificity to unique target sites, and are fused to a cleavage domain such as FokI (Cermak, et al., *Nucleic Acids Research*, 39(12) (2011), Page e82, doi/10.1093/nar/gkr218).

Repair of TALEN-induced double stranded breaks generally occurs by non-homologous end joining (NHEJ) and results in mutations that knock out gene function. TALENs can also be combined with a donor template for HDR as described below. A strength of the TALEN approach is that any site can be targeted, and it is not limited by the PAM sites that are needed for Cas targeting. TALEN approaches are fully compatible with the cenh3 haploid inducer system, and the two technologies can be usefully combined to facilitate genotype-independent gene editing.

See also, Cermak, et al, *Nucl. Acids Res.* 1-11 (2011), US Published Application No. 2011/0145940, Miller et al., *Nature Biotechnol* 29: 143 (2011) for further TALEN design considerations.

b. Gene Altering DNA Sequences

The nuclease activity of the genome editing systems described herein cleave target DNA to produce single or double strand breaks in the target DNA. Double strand breaks can be repaired by the cell in one of at least two ways: non-homologous end joining (NHEJ), and homology-directed repair (HDR). In non-homologous end joining, the double-strand breaks are repaired by direct ligation of the break ends to one another. As such, no new nucleic acid material is inserted into the site, although some nucleic acid material may be lost or gained during the repair process, resulting in a small deletions or insertions that can knock out gene function. In homology-directed repair, a donor polynucleotide with homology to the cleaved target DNA sequence is used as a template for repair of the cleaved target DNA sequence, resulting in the transfer of genetic information from a donor polynucleotide to the target DNA. As such, new nucleic acid material can be inserted/copied into the site.

Therefore, in some embodiments, the inducer plant optionally includes a donor polynucleotide, for example as a segment of the inducer plant's genome. The modifications of the target plant's DNA due to homology-directed repair can be used to induce gene correction, gene replacement, gene tagging, transgene insertion, nucleotide deletion, gene disruption, gene mutation, etc.

In this application, the donor polynucleotide sequence generally includes regions of sequence homology to the target DNA sequence known as homology arms. The sequence between the homology arms can be natural or engineered sequence that introduces new features such as tags, promoter motifs, expressed protein motifs, or other sequences of interest. During HDR, the homology arms are used to guide the repair of the double stranded break, resulting in insertion of the new sequence into the target site.

In applications in which it is desirable to insert a polynucleotide sequence into a target DNA sequence, a donor sequence to be inserted is also provided by the inducer plant's genome. The donor sequence with homology arms can be in the form of a second DNA construct or construct component (Shi, et al., *Plant Biotechnology Journal*, 15:207-216 (2017)), or a construct that expresses RNA that can be used as donor template for repair (Li, et al., *Nature Biotechnology*, 37:445-450 (2019)).

When insertion of the donor sequence for purposes of altering the genomic sequence of the target plant, the donor sequence is typically not identical to the genomic sequence that it replaces. Rather, the donor sequence may contain at least one or more single base changes, insertions, deletions, inversions or rearrangements with respect to the genomic sequence, so long as sufficient homology is present to support homology-directed repair. In some embodiments, the donor sequence includes a non-homologous sequence flanked by two regions of homology, such that homology-directed repair between the target DNA region and the two flanking sequences results in insertion of the non-homologous sequence at the target region.

The donor sequence can include restriction sites, nucleotide polymorphisms, selectable markers (e.g., drug resistance genes, fluorescent proteins, enzymes etc.), etc., relative to the genomic sequence which can be used to assess for successful insertion of the donor sequence at the cleavage site or in some cases may be used for other purposes (e.g., to signify expression at the targeted genomic locus). In some cases, if located in a coding region, such nucleotide sequence differences will not change the amino acid sequence, or will make silent amino acid changes (i.e., changes which do not affect the structure or function of the protein). Alternatively, these sequence differences may include flanking recombination sequences such as FLPs, loxP sequences, or the like, that can be activated at a later time for removal of the marker sequence.

It is believed that all of the currently employed gene editing methods, including CRISPR/Cas9, zinc fingers, TALENs, their combination with base editors, and their use to direct the insertion of altered DNA sequences by HDR, are compatible with the cenh3 haploid inducer system. The value of the cenh3 haploid inducer in this context is to facilitate the transfer of gene editing machinery from an easily transformable line into elite germplasm in a rapid and efficient manner.

III. Methods of Use

A. Haploid Induction

Methods for haploid induction are provided. The disclosed haploid induction methods typically include a cross between the line to be induced and a haploid inducer line. As discussed above, the haploid inducer is typically a heterozygous cenh3 null plant.

Haploid plants are produced by making crosses between the haploid inducer and virtually any inbred, hybrid, or other germplasm of interest. Haploids are produced when the chromosomes from the haploid inducer plant are not maintained through the first cell divisions of the embryos. The resulting phenotype is not fully penetrant, with some ovules containing haploid embryos, and others containing diploid embryos, aneuploid embryos, chimeric embryos, or aborted embryos. After haploid induction, haploid embryos or seed are typically segregated from diploid and aneuploid siblings using a phenotypic or genetic marker screen and grown into haploid plants. These plants are then converted via chemical manipulation (e.g., using an anti-microtubule agent such as colchicine) into doubled haploid ("DH") plants which then produce inbred seed.

Plant breeding is greatly facilitated by the use of doubled haploid (DH) plants. The production of DH plants enables plant breeders to obtain inbred lines without multi-generational inbreeding, thus decreasing the time needed to produce homozygous plants.

The haploid inducer is crossed (either as the male or female) to a targeted line to generate haploid progeny. The result is a haploid embryo or plant or seed that contains the chromosome set only from the non-inducer parent.

If the inducer is used as the male, the recovered progeny will have the cytoplasm of the targeted line. If the cytoplasm of the inducer is desired (for example to obtain male sterile cytoplasm), the haploid inducer can be used as the female.

Additional steps can include haploid identification techniques, and subsequent chromosome doubling techniques such as, but not limited to, those described by Prigge and Melchinger ("Production of Haploids and Doubled Haploids," in Maize Plant Cell Culture Protocols, Methods in Molecular Biology, Volume 877, pp. 161-172, 2012) and others, which include, for example, use of colchicine, pronamide, dithipyr, trifluralin, or another known anti-microtubule agent or other mitotic inhibitor. This line can then be directly used in downstream breeding programs.

The ease of use should make it particularly versatile when combined with other technologies that are built upon haploids. One such application is synthetic apornixis, where plants are engineered to skip neiosis and produce diploid gametes; when these lines are crossed to a haploid inducer, the resulting progeny are identical in genotype to the parent (Mariiuthu, et al., Science, 331(6019):876 (2011)). Another application is the field of chromosome engineering, where the haploid inducer is exploited to quickly move small, engineered, or fully synthetic chromosomes from one line to another (Birchler, et al., Current Opinion in Plant Biolog.y, 19:76-80 (2014).

B. Gene Editing in Monocots

1. Methods of Gene Editing

Methods of simultaneous haploid induction and gene editing are also provided. The disclosed methods typically include a cross between the line to be induced and a haploid inducer line. As introduced above, the haploid inducer is typically a heterozygous cenh3 null plant, and also encodes gene editing machinery of the CRISPR/Cas9, zinc finger, TALEN types, either alone or in combination with base editor enzymes and/or donor molecules that allow for HDR and gene replacement or modification.

In simultaneous editing plus haploid induction, rapid and cost-effective production of edited crops and elite lines is possible without tissue culture. The line that receives the edits can be elite germplasm, and the editing machinery itself would be eliminated during the haploid induction process. At the same time, edited doubled haploid lines are produced.

The gene editing machinery is delivered via the inducer line. The DNA, RNA, and proteins that make up the gene editing machinery are encoded by and are present in the inducer line. Typically, the gene editing machinery are been stably inserted in the inducer, for example, via bombardment or agrobacterium mediated transformation. The transgenic haploid inducer lines expressing editing machinery can be used as either pollen donors or acceptors in interspecific or intergeneric wide crosses for haploid induction and simultaneous genome editing.

The haploid inducer is crossed (either as the male or female) to a targeted line to generate haploid progeny. After fertilization, edits are made by the editing machinery in the non-inducer target genes prior to or during elimination of the inducer chromosomes. The result is a haploid embryo or plant or seed that contains the chromosome set only from the non-inducer parent, where that chromosome set contains DNA sequences that have been edited.

The promoter(s) used in the endonuclease construct typically result in endonuclease expression before fertilization, during the first couple of cell divisions, or a combination thereof. By using the haploid inducer as the female, if the endonuclease is expressed in the egg before pollination and during the first stages of cell development, the endonuclease can immediately begin mutating the target sequence upon pollination and continue mutating the target sequence before the haploid inducer genome is lost from the cell. In the first stages of mitosis, before the haploid inducer genome is eliminated, the targeted endonuclease induces targeted DNA strand break(s) in the DNA of the target line. These breaks are repaired by NJEH to create small insertions or deletions, or corrected by HDR, depending on the gene editing application.

The haploid progeny genomes can be doubled before or after the progeny are screened for the mutation(s). Once the genomes of these haploid individuals are doubled, the individuals can be grown out and self-pollinated to produce doubled haploid seed. Different mutations may be produced, and mutation events can be evaluated to determine if the mutation(s) obtained have the desired result. The disclosed methods may be conducted on all (or many) of the monocot lines that a breeder plans to use as parents for breeding. If a breeder develops populations using lines that have a desirable mutation(s) at all targeted loci, the populations do not segregate for the desirable mutation(s). Thus, the breeding efforts are simplified by not having to select for the presence of the desirable mutation(s).

The methods can produce doubled haploid individuals with the targeted mutation(s) without the time and expense of backcrossing in a desired targeted mutation into the targeted line. The cenh3 haploid inducer is genetically dominant. When the cenh3 null is crossed to any line, the resulting $F_1$ itself becomes a haploid inducer. The $F_1$ individual containing the cenh3 null and gene editing machinery can be crossed to hundreds or even thousands of elite lines particularly where the inducer stock line is used as the male. In some embodiments, doubled haploid individuals from multiple elite lines, all with the targeted mutation(s) are produced in less than one year.

In some embodiments, the inducer line can target 2, 3, 4, 5 or more mutations by including, for example, multiple endonuclease transgenes, and/or gRNAs, and/or donor sequences, etc.

Recovered doubled haploid individuals may not have all of the desired mutations. In some embodiments, where multiple mutations are desired, doubled haploid progeny with single mutations can be crossed together, and the $F_2$ progeny can be screened for individuals that are homozygous for all desired mutations.

If the inducer is used as the male, the recovered progeny will have the cytoplasm of the targeted line. If the cytoplasm of the inducer is desired (for example to obtain male sterile cytoplasm), the haploid inducer can be used as the female. If the cytoplasm of the targeted line is desired, crosses can be made between the non-mutated version of the targeted line (as the female) and the mutated version of the targeted line (as the male).

2. Types of Gene Editing

As introduced above, suitable gene editing systems include, but are not limited to, those that cause mutations or base edits, and targeted sequence insertion by HDR. It is believed that any form of stable gene editing process, whether it be through CRISPR/Cas9, zinc fingers, or TAL-ENs can be combined with the cenh3 null to modify the genome of a target line. By using one Cas9 nuclease and multiple gRNAs, more than one site can be targeted and altered simultaneously.

When an active Cas protein is targeted to a locus and no donor template is provided, one possible outcome is small deletions or insertions that are created during the NHEJ repair process. If the targeted location is properly selected, the mutation can create a frameshift in the coding sequence and abolish the function of the gene, or alter the promoter to change the expression pattern. If the intent is to knock out expression, multiple gRNAs are frequently targeted to several regions of the coding sequence. If multiple gRNAs are targeted to the promoter, dramatic and useful changes in gene expression can result (Rodriguez, et al., *Cell*, 171(2): 470-80 (2017)).

Targeted mutagenesis of DNA sequence can also be achieved through direct conversion of one DNA base to another without requiring double stranded breaks (DSBs).

For example, cytidine deaminase APOBEC1, adenine deaminase, and other enhancing components like Uracil DNA glycosylase (UDG) can be fused to Cas9 (A840H) nickase or nuclease-inactivated dead Cas9 (dCa9) to direct editing of DNA sequence without introducing double strand DNA breaks (Komor et al., *Nature*, 533:420-424 (2016) doi:10.1038/nature17946; Gaudelli et al., *Nature*, 551:464-471 (2017) doi:10.1038/nature24644; Komor et al., *Science Advances*, 3(8) eaao4774 (2017), DOI: 10.1126/sciadv.aao4774). This kind of base editor machinery can also be delivered through haploid induction line to induce base editing in target sequences directly in other varieties.

HDR, which is an alternative means of repairing DSBs in chromosomes, is a mechanism for engineering plant genomes that facilitates more subtle DNA sequence modifications, including DNA correction, targeted knock-in or replacement, or any type of desired mutation. HDR occurs during cell division (Ceccaldi, et al., Trends Cell Biol, 26(1):52-64 (2016). doi: 10.1016/j.tcb.2015.07.009) and may be particularly active during the rapid cell divisions of the young embryo. In support of this, data presented below indicate that HDR may be responsible for the mutation in the plant produced by simultaneous haploid induction and pass-through gene editing of Example 2.

Thus, it is believed that not only can in vivo haploid induction system be used to introduce protein, RNA or DNA for cleavage or conversion of target sequence, it can also be used, along with an appropriate repair template, to introduce precise sequence changes to regions targeted for gene editing.

The template DNA can be inserted into the inducer line genome carrying genome editing machinery such as CRISPR-Cas9 system, either in the same transgenic locus or different locus. When both Cas9-sgRNA and template DNA are present in the induced haploid embryos, cleavage of the target sequence will result in repair of the chromosomal break with the homologous transgenic DNA sequence as template.

Transgenes can be introduced into a DSB if the provided template contains the transgene flanked by sequences that are homologous to the sequences on either side of the DSB (homology arms, see, Shukla et al., *Nature*, 459:437-441, (2009)). A transgenic event (e.g., to insert a gene of interest) is crossed into the haploid inducer line. An endonuclease gene can be used to target the relative position of the transgene in a non-transgenic line. The transgenic event to be inserted needs to be flanked on both sides by DNA sequences homologous to the DNA flanking the target site. When the haploid inducer is crossed to the targeted line, the endonuclease will cause a double strand break at the target site. If the targeted line's DNA is repaired by HDR using the haploid inducer stock line's DNA (and transgene) as the template, the targeted line DNA "repairs" the double strand break by putting the transgene sequence in the double strand break site. Thus, the disclosed methods may be used to place transgenes into targeted lines without having to backcross.

The disclosed compositions and methods can be further understood through the following numbered paragraphs.

1. A monocot haploid inducer plant heterozygous for centromeric histone 3 (CenH3) comprising diploid plant cells comprising only one allele encoding functional CENH3 protein.

2. The monocot plant of paragraph 1, wherein the diploid plant cells comprise one CenH3 allele encoding non-functional CENH3 protein.

3. The monocot plant of paragraph 2, wherein the allele encoding non-functional CENH3 protein is a protein null allele.

4. The monocot plant of paragraphs 2 or 3, wherein the allele encoding non-functional CENH3 protein is an RNA null allele.

5. The monocot plant of any one of paragraphs 1-4, wherein the allele encoding non-functional CENH3 protein is caused by frameshift mutation that creates a stop codon that abolishes function.

6. The monocot plant of any one of paragraphs 1-5, wherein the endogenous CenH3 loci on a first diploid chromosome is partially or completely deleted.

7. The monocot plant of any one of paragraphs 1-6, wherein the endogenous CenH3 loci on a second diploid chromosome is intact.

8. The monocot plant of any one of paragraphs 1-7, wherein the functional CENH3 protein is wildtype CENH3 protein.

9. The monocot plant of any one of paragraphs 1-8, wherein the plant lacks a chromosomally integrated or extrachromosomal transgene encoding wildtype CenH3.

10. The monocot plant of any one of paragraphs 1-9, wherein the plant lacks a chromosomally integrated or extrachromosomal transgene encoding a CENH3 variant or fusion protein.

11. The monocot plant of paragraph 10, wherein the fusion protein that is lacking from the plant comprises green fluorescent protein.

12. The monocot plant of paragraphs 10 or 11, wherein the fusion protein that is lacking from the plant is GFP-tailswap.

13. The monocot plant of any one of paragraphs 1-12, wherein the sperm or eggs are have less CENH3 than a CENH3 homozygous wild type plant's sperm or eggs, optionally wherein the sperm or egg have less than 50% CENH3 than a wild type plant's sperm or eggs, preferably, wherein the sperm or egg have between about 50% and 10%, for example, 50%, 25%, or 12.5% of the CENH3 than a wild type plant's sperm or eggs.

14. The monocot plant of any one of paragraphs 1-13, wherein the plant is maize, wheat, rice, sorghum, barley, oats, triticale, rye, pearl millet, finger millet, proso millet, foxtail millet, banana, bamboo, sugar cane, switchgrass, Miscanthus, asparagus, onion, garlic, chives, or yam.

15. The monocot plant of paragraph 14, wherein the plant is maize.

16. The monocot plant of any one of paragraphs 1-15, further comprising an exogenous site-directed nuclease expressed by cells of the monocot plant.

17. The monocot plant of paragraph 16, wherein the diploid plant cells comprise one CenH3 allele encoding non-functional CENH3 protein.

18. The monocot plant of paragraph 17, wherein the allele encoding non-functional CENH3 protein is a protein null allele.

19. The monocot plant of paragraphs 17 or 18, wherein the allele encoding non-functional CENH3 protein is an RNA null allele.

20. The monocot plant of any one of paragraphs 16-19, wherein the allele encoding non-functional CENH3 protein is caused by frameshift mutation that creates a stop codon that abolishes function.

21. The monocot plant of any one of paragraphs 16-20, wherein the endogenous CenH3 loci on a first diploid chromosome is partially or completely deleted.

22. The monocot plant of any one of paragraphs 16-21, wherein the endogenous CenH3 loci on a second diploid chromosome is intact.

23. The monocot plant of any one of paragraphs 16-22, wherein the functional CENH3 protein is wildtype CENH3 protein.

24. The monocot plant of any one of paragraphs 16-23, wherein the plant lacks a chromosomally integrated or extrachromosomal transgene encoding wildtype CenH3.

25. The monocot plant of any one of paragraphs 16-24, wherein the plant lacks a chromosomally integrated or extrachromosomal transgene encoding a CENH3 variant or fusion protein.

26. The monocot plant of paragraph 25, wherein the fusion protein that is lacking from the plant comprises green fluorescent protein.

27. The monocot plant of paragraphs 25 or 26, wherein the fusion protein that is lacking from the plant is GFP-tailswap.

28. The monocot plant of any one of paragraphs 16-27, wherein the sperm or eggs are have less CENH3 than a CENH3 homozygous wild type plant's sperm or eggs, optionally wherein the sperm or egg have less than 50% CENH3 than a wild type plant's sperm or eggs, preferably, wherein the sperm or egg have between about 50% and 10%, for example, 50%, 25%, or 12.5% of the CENH3 than a wild type plant's sperm or eggs.

29. The monocot plant of any one of paragraphs 26-28, wherein the site-directed nuclease is stably expressed by cells of the monocot plant.

30. The monocot plant of paragraph 29, wherein the site directed nuclease is a meganuclease (MN), zinc-finger nuclease (ZFN), transcription-activator like effector nuclease (TALEN), or a CRISPR-based nuclease optionally wherein the nuclease is selected from Cas9 nuclease, Cfp1 nuclease, dCas9-FokI, dCpf1-FokI, chimeric Cas9-cytidine deaminase, chimeric Cas9-adenine deaminase, chimeric FEN1-FokI, and Mega-TALs, a nickase Cas9 (nCas9), chimeric dCas9 non-FokI nuclease, dCpf1 non-FokI nuclease, chimeric Cpf1-cytidine deaminase, and Cpf1-adenine deaminase.

31. The monocot plant of paragraphs 29 or 30, wherein the plant's genome comprises a heterologous nucleic acid construct encoding the nuclease.

32. The monocot plant of any one of paragraphs 16-31, further comprising a guide RNA expressed by cells of the monocot plant.

33. The monocot plant of paragraphs 29 or 30, wherein the plant's genome comprises a heterologous nucleic acid construct encoding the gRNA.

34. The monocot plant of any one of paragraphs 16-33, wherein the plant's genome comprises a donor nucleic acid sequence to be introduced by recombination at a cleavage site induced by the nuclease.

35. The monocot plant of any one of paragraphs 16-34, wherein the plant is maize, wheat, rice, sorghum, barley, oats, triticale, rye, pearl millet, finger millet, proso millet, foxtail millet, banana, bamboo, sugar cane, switchgrass, Miscanthus, asparagus, onion, garlic, chives, or yam.

36. An egg cell formed by the plant of any one of paragraphs 1-15, the egg cell lacking the one allele encoding functional CENH3 protein and comprising no more than about 12.5% functional CENH3 protein relative to a corresponding egg cell formed by a CenH3 homozygous plant.

37. A sperm cell formed by the plant of any one of paragraphs 1-15, the sperm cell lacking the one allele encoding functional CENH3 protein and comprising no more than about 25% functional CENH3 protein relative to a corresponding egg cell formed by a CenH3 homozygous plant.

38. An egg cell formed by the plant of any one of paragraphs 16-35, the egg cell lacking the one allele encoding functional CENH3 protein and comprising no more than about 12.5% functional CENH3 protein relative to a corresponding egg cell formed by a CenH3 homozygous plant.

39. A sperm cell formed by the plant of any one of paragraphs 16-35, the sperm cell lacking the one allele encoding functional CENH3 protein and comprising no more than about 25% functional CENH3 protein relative to a corresponding egg cell formed by a CenH3 homozygous plant.

40. A method of inducing formation of a target haploid monocot plant comprising pollinating a parent monocot target plant with pollen from the monocot haploid inducer plant of any one of paragraphs 1-15; and selecting at least one haploid progeny produced by the pollination.

41. A method of inducing formation of a target haploid monocot plant comprising pollinating the monocot haploid inducer plant of any one of paragraphs 1-15 with pollen from a parent monocot target plant; and selecting at least one haploid progeny produced by the pollination.

42. The method of paragraphs 40 or 41, further comprising chromosome doubling of the selected haploid progeny.

43. The method of paragraph 42, wherein chromosome doubling is spontaneous or induced by a chromosome doubling agent optionally selected from colchicine, pronamide, dithipyr, trifluralin, or another anti-microtubule agent.

44. The method of any one of paragraphs 40-43, wherein the monocot target plant is selected from maize, wheat, rice, sorghum, barley, oats, triticale, rye, pearl millet, finger millet, proso millet, foxtail millet, banana, bamboo, sugar cane, switchgrass, Miscanthus, asparagus, onion, garlic, chives, or yam.

45. A method of modifying the genome of a monocot target plant comprising inducing formation of a target haploid monocot plant comprising pollinating a parent monocot target plant with pollen from the monocot haploid inducer plant of any one of paragraphs 16-35, and selecting at least one haploid progeny produced by the pollination, wherein the haploid progeny comprises the genome of the monocot target plant but not the monocot haploid inducer plant, and the genome of the haploid progeny has been modified by the site directed nuclease and optionally at least one guide RNA delivered by the monocot haploid inducer plant.

46. A method of modifying the genome of a monocot target plant comprising inducing formation of a target haploid monocot plant comprising pollinating the monocot haploid inducer plant of any one of paragraphs 16-35 with pollen from a parent monocot target plant, and selecting at least one haploid progeny produced by the pollination, wherein the haploid progeny comprises the genome of the monocot target plant but not the monocot haploid inducer plant, and the genome of the haploid progeny has been modified by the site directed nuclease and optionally at least one guide RNA delivered by the monocot haploid inducer plant 47. The method of paragraphs 45 or 46, further comprising chromosome doubling of the selected haploid progeny.

48. The method of paragraph 47, wherein chromosome doubling is spontaneous or induced by a chromosome doubling agent optionally selected from colchicine, pronamide, dithipyr, trifluralin, or another anti-microtubule agent.

49. The method of any one of paragraphs 45-48, wherein the monocot target plant is selected from maize, wheat, rice, sorghum, barley, oats, triticale, rye, pearl millet, finger millet, proso millet, foxtail millet, banana, bamboo, sugar cane, switchgrass, Miscanthus, asparagus, onion, garlic, chives, or yam.

EXAMPLES

Example 1: Preparation of Maize Cenh3 Null Mutant, and Use Thereof for Haploid Induction

Materials and Methods

Plant materials

The gl1, gl8, and cenh3-mu1015598 transposon insertion lines were obtained from the Maize Genetics Cooperation Stock Center, Urbana, Illinois. The cenh3-mu1015598 allele is one of several mutations in the UFMu-01386 stock line. All plants were grown in the University of Georgia Plant Biology greenhouses.

Construct Preparation and Transformation

The Ubi-Cas9 construct contains 1991 bp of the maize polyubiquitin promoter (GenBank: 594464.1) driving a maize codon-optimized version of Cas9 terminated by the Nos terminator.

The gRNA-ImmuneCENH3 construct contains two components, a guide RNA module and the ImmuneCENH3 gene. The guide RNA portion contains the maize U6 promoter (Svitashev, et al., *Plant Physiol.* 169, 931-945 (2015)) driving a guide RNA (TCCCGCAGCGCTACAGTCCC) (SEQ ID NO:1) terminated by the PolIII terminator TTTTTTTT. The ImmuneCENH3 portion contains 6455 bp of the native CENH3 gene (coordinates Chr6:166705239-166711693 on Zm-B73-REFERENCE-NAM-5.0) but has five silent codon changes in the gRNA target area (CCAGGTACGGTCGCCCTGCGCGA) (SEQ ID NO:2). The promoter includes 2184 bp of sequence upstream of the ATG.

To create the gRNA-TailswapCENH3 construct, the natural 5' UTR of CENH3 was retained and a codon-optimize GFP sequence was inserted at the ATG of ImmuneCENH3. This was followed by a linker sequence ATGGATGAAC-TATACAAGGGCGGAGGCGGTGGAGGCGTCGAC (SEQ ID NO:3) and the tail sequence of the maize H3.3 gene (Genbank NM_001294303.2) including its intron, fused to the native CENH3 gene 3 bp upstream of the guide RNA target area. The Arabidopsis GFP-tailswap transgene also includes the H-13.3 portion. The construct was based on the sequence of Arabidopsis GFP-tailswap obtained from the Comai laboratory.

The three constructs were synthesized by GenScript (www.genscript.com) and cloned into the binary vector pTF101.1 (Paz, et al., *Euphytica* 136, 167-179 (2004)). To generate the cenh3 mutation, transgenic lines carrying Ubi-Cas9 were crossed with lines carrying gRNA-ImmuneCENH3.

DNA Extraction, Genotyping and Sequence Analysis

For standard leaf genotyping, genomic DNA was prepared using a CTAB protocol (Clarke, Cold Spring Harbor Protocols vol. 2009 db.prot5177-pdb.prot5177 (2009)). Endosperm tissue was collected after the kernels had germinated and the glossy phenotype could be distinguished.

Embryos and pericarps were removed with forceps, and the endosperm ground to a powder with a mortar and pestle. The endosperm DNA was extracted with the IBI Plant Genomic DNA Mini Kit (IBI Scientific IB47231).

To identify the presence of ImmuneCENH3 and Cas9 in transgenic lines, primers CENH3-F2 and CENH3-R3 were used to amplify ImmuneCENH3, and primers Cas9-F1 and Cas9-R1 were used to amplify Cas9 (Table 1). To identify the original cenh3 mutation in Cas9 plants, PCR was carried out using the Phusion High-Fidelity PCR Kit (New England Biolabs, Ipswich, MA) with primers CENH3-F1 and CENH3-R1 in Table 1 (SEQ ID NOS:4-14, in descending order as they appear in the table).

mM NaCl, 80 mM KCl, 0.5 mM spermine, 15 mM 2-mer-captoethanol, 0.1 mM PMSF, 0.1% Triton X-100). After chopping, the mixture was filtered through a 40 m cell strainer twice. The nuclei were stained with 4,6-diamidino-2-phenylindole and loaded into flow cytometers hosted by the CTEGD Cytometry Shared Resource Lab at the University of Georgia.

Chromosome Spreads

Chromosome analysis was carried out as described in (Dawe, et al., *Cell* 173, 839-850.e18 (2018)). Briefly, root tips were collected from the haploid and diploid plants, incubated in a chamber with nitrous oxide for three hours, and fixed with 90% acetic acid. Root tips were cut with a

TABLE 1

Primers Used.

| Gene: | Primer sequence | SEQ ID NO: | Purpose |
|---|---|---|---|
| CENH3-F1 | TGCAAGATGAGGGCGAATGTG | 4 | Genotyping on native CENH3 and Immune CENH3 |
| CENH3-R1 | TACTTCCTGATCTCCCGCAGC | 5 | Genotyping on native CENH3 and not Immune CENH3 |
| CENH3-F2 | GGCTGCTCTTACTTGCTTGC | 6 | Genotyping on native CENH3 and ImmuneCENH3 |
| CENH3-R2 | CGCTCTACTTTCCCGTTTGTTAC | 7 | Genotyping on native CENH3 and Immune CENH3 |
| CENH3-R3 | TACTTCCTGATCTCGCGCAGGGCG | 8 | Genotyping on ImmuneCENH3 and not native CENH3 |
| Cas9-F1 | ACGAGAAGTACCCGACAATCTACC | 9 | Genotyping on Cas9 |
| Cas9-R1 | TGATTTGAAGTTCGGCGTCAGG | 10 | Genotyping on Cas9 |
| CENH3-F4 | CGCTCGAACTGGAGCTTCTT | 11 | Genotyping on cenh3::mu |
| CENH3-R4 | AGGTTGGCAGGTAGCCGTTA | 12 | Genotyping on cenh3::mu |
| Mu1 | GCCTCTATTTCGTCGAATCCG | 13 | Genotyping on cenh3::mu |
| Mu2 | GCCTCCATTTCGTCGAATCCC | 14 | Genotyping on cenh3::mu |

The PCR products were either directly Sanger sequenced or cloned using a TOPO TA cloning kit (Thermo Fisher #K457501) and then Sanger sequenced.

In lines that lack ImmuneCENH3, the cenh3 null allele was differentiated from the native CENH3 allele by PCR and restriction enzyme digestion. PCR amplifies a 496 bp PCR product using primers CENH3-F2 and CENH3-R2. When this product is digested with the restriction endonuclease AlwNI (New England Biolabs), the wild type allele is cleaved into two pieces of size 284 bp and 212 bp while the mutant cenh3 allele is not cleaved.

The cenh3-mu1015598 allele was scored using the primers CENH3-F4, CENH3-R4 and Mumix (a 1:1 mix of the two primers Mu1 and Mu2 in Table 1). The wild type allele is amplified with CENH3-F4 and CENH3-R4 while the Mu allele is amplified with CENH3-F4 and Mumix.

Ploidy Evaluation

Progeny from +/cenh3 crosses were grown indoors under grow lights for 10-13 days and water sprayed on the seedlings to identify the glossy phenotype. All glossy plants were subsequently assayed by flow cytometry. For each individual, about 1 g of flash-frozen leaves or roots were collected and chopped into 1.5 ml of pre-chilled nuclei extraction buffer (2 mM EDTA, 15 mM Tris-HCl pH 7.5, 20 razor blade and digested in an enzyme solution (1% pecto-lyase Y-23, 2% cellulase Onozuka R-10) at 37° C. for 50 minutes. The root section was washed in ethanol then immersed in 90% acetic acid. A metal pick was used to crush the roots tips and 10 μl of the cell suspension was dropped onto microscope slides. Slides were dried and mounted with a glass coverslip using ProLong Gold with DAPI (Thermo Fisher Cat #P36931). Slides were imaged on a Zeiss Axio Imager.M1 fluorescence microscope with a 63X Plan-APO Chromat oil objective, and slidebook software (Intelligent Imaging Innovations, Denver, CO, USA) used to analyze the data.

Skim Sequencing of Haploids and Aneuploids

For each sample, 12 ng/pl DNA was sonicated in a 100 μl volume with a Diagenode Bioruptor for seven minutes on high setting with 30-second on-off intervals, yielding fragments averaging about 500 bp in length. DNA sequencing libraries were prepared using the KAPA Hyperprep Kit (KK8502) with KAPA single-indexed adapters (KK8700). 600 ng of sonicated DNA was used as input for each sample, and 3 cycles of PCR were used to amplify libraries. 150-nt Illumina sequencing reads were adapter-trimmed and quality-filtered using Cutadapt version 1.9.1 (Martin, et al., *EMBnet.journal* vol. 17 10 (2011)) with parameters as follows: "-q 20 -a AGATCGGAAGAGC -e 0.05 -O 1-m 50" (SEQ ID NO:15). Reads were aligned to Zm-B73-REFERENCE-NAM-5.0 using BWA-mem version 0.7.15 in single-end mode with default parameters (Li, & Durbin, Bioinformatics vol. 25 1754-1760 (2009)). Read coverage was visualized using IGVTools version 2.3.98 (Thorvaldsd6ttir, et al., *Brief Bioinform.* 14, 178-192 (2013)) with coverage calculated on 25 Mb intervals.

Results

Doubled haploid breeding is widely used to accelerate the production of new inbred lines (Kalinowska, et al., *Theor. Appi. Genet.* 132, 593-605 (2019)). One common approach, used throughout the maize breeding industry, involves creating haploids with mutants that interfere with fertilization (Kelliher, et al., *Nature* 542, 105-109 (2017), Liu, et al., *Mol. Plant* 10, 520-522 (2017), Gilles, et al., *EMBO J.* 36, 707-717 (2017), Yao, et al., *Nat Plants* 4, 530-533 (2018), Zhong, et al., *Nat Plants* 6, 466-472 (2020)). An entirely different method of inducing haploids was pioneered by Simon Chan and colleagues, who showed that crossing *Arabidopsis* lines with a structurally altered Centromeric Histone H3 (CENH3) protein yielded haploids and aneuploids at frequencies as high as 25-45% (Ravi and Chan, *Nature* 464, 615-618 (2010)). CENH3 is a histone variant that defines centromere location and recruits overlying kinetochore proteins (Cheeseman & Desai, *Nat. Rev. Mol. Cell Biol.* 9, 33-46 (2008), Black & Bassett, *Curr. Opin. Cell Biol.* 20, 91-100 (2008)). The original study involved a construct called GFP-tailswap where the N-terminal tail of CENH3 was modified with a GFP tag, however point mutations and small deletions of CENI-13 can also induce haploids at similar frequencies (Karimi-Ashtiyani, et al., *Proc. Natl. Acad. Sci. U.S.A* 112, 11211-11216 (2015), Kuppu, et al., *PLoS Genet.* 11, e1005494 (2015), Kuppu, et al., *Plant Biotechnol. J.* (2020) doi:10.1111/pbi.13365). Outside of Arabidopsis, centromere-mediated haploid induction has proven to be less effective, generally producing <1% haploids (Kalinowska, et al., *Theor. Appl. Genet.* 132, 593-605 (2019)).

The current study was designed to investigate the mechanism of centromere-mediated haploid induction in maize, initially using the GFP-tailswap method. However, this approach is complicated by the fact that it needed both a mutant of native cenh3 and a functional GFP-tailswap transgene that complements the mutant. Another group had already shown some success using an existing maize mutant (cenh3-mu1015598) caused by a Robertsons Mutator (Mu) insertion in the 5' UTR of the gene (Kelliher, et al., *Front. Plant Sci.* 7, 414 (2016), Feng, et al., *Plant J.* (2019) doi:10.1111/tpj.14606)). They crossed GFP-tailswap into the cenh3-mu1015598 background and observed an average of 0.86% haploids when crossed as a male and no haploids when crossed as a female (Kelliher, et al., *Front. Plant Sci.* 7, 414 (2016)). cenh3-mu1015598 was obtained and three heterozygous plants were self-crossed. Genotyping revealed that two ears segregated a low frequency of homozygous mutants that grew to various states of maturity (Table 2).

TABLE 2

The cenh3-mu1015598 mutant is not a null *.

| Cross | # seedlings | expected WT:het:hom | observed WT:het:hom |
|---|---|---|---|
| +/cenh3-mu1015598-1 ⊗ | 76 | 19:38:19 | 23:44:8 |
| +/cenh3-mu1015598-2 ⊗ | 37 | 9:19:9 | 6:25:6 |
| +/cenh3-mu1015598-3 ⊗ | 25 | 6:13:6 | 8:18:0 |

* WT indicates wild type, het indicates +/cenh3-mu1015598 heterozygote, and hom indicates cenh3-mu1015598/cenh3-mu1015598 homozygote. Note that the first two plants yielded homozygous cenh3-mu1015598 progeny.

The recovery of homozygous mutants indicates that cenh3-mu1015598 is not a null, and that the prior results may have been confounded by a low level of wild type CENH3 expression. The variable penetrance of the cenh3-mu1015598 allele can be explained by the fact that Mu elements can promote low levels of expression when inserted into 5' UTR regions (Barkan & Martienssen, *Proc. Natl. Acad. Sci. U.S.A* 88, 3502-3506 (1991)).

To overcome the selection against true null cenh3 alleles, a cenh3 null was created using a two-construct CRISPR/Cas9 approach. One line was transformed with a simple construct expressing Cas9 driven by an Ubiquitin promoter. A second was transformed with a construct expressing a gRNA targeting the fourth exon of the native CENH3 gene and an "ImmuneCENH3" gene that contains a full-length native CENH3 gene with five silent nucleotide changes in the gRNA target area (FIG. 1A, 1B). After the two lines were crossed together, Cas9 generated mutations in the native CENH3 gene but left the transgene unaffected. A cenh3 allele with a single nucleotide deletion was chosen that causes an immediate stop codon in the N-terminal tail of CENH3 (FIG. 1C). In the presence of ImmuneCENH3, the cenh3 mutation segregates as a simple Mendelian recessive trait (Table 3).

TABLE 3

Segregation of cenh3 in ImmuneCENH3 and TailswapCENH3 backgrounds*.

| Cross | transgene genotypes | cenh3 genotypes |
|---|---|---|
| +/ImmuneCENH3, | +/ImmuneCENH3 or | +/+ (54) |
| +/cenh3 | ImmuneCENH3/ImmuneCENH3 | +/cenh3 (75) |
| ⊗ | (172) | cenh3/cenh3 (43) |
| | +/+ (33) | |
| +/TailswapCENH3, | +/TailswapCENH3 or | +/+ (47) |
| +/cenh3 | TailswapCENH3/TailswapCENH3 | +/cenh3 (6) |
| ⊗ | (56) | cenh3/cenh3 (0) |
| | +/+ (16) | |

*Numbers in parentheses show the number of plants of each genotype.

Transgenics were then created with TailswapCENH3, a close replica of the Arabidopsis GFP-tailswap construct, and it was crossed to the cenh3 mutation. Plants that contained TailswapCENH3 and homozygous for cenh3 (Table3) were not obtained, indicating that the transgene does not complement a true null (FIG. 4A).

During the course of these studies, it was discovered that cenh3 was occasionally transmitted in the absence of ImmuneCENH3. By crossing to wild type lines, a simple segregating cenh3 line was obtained that lacked both of the original transgenes. Among selfed progeny from a +Icenh3 line there were 163+/+wild type individuals, 55+/cenh3 heterozygotes, and zero cenh3/cenh3 homozygotes, indicating that the mutant is homozygous lethal and poorly transmitted through gametophytes. Reciprocal crosses between +Icenh3 heterozygotes and wild type plants were also carried out. A Mendelian trait is normally transmitted to 50% of testeross progeny, however it was observed that only 12.1% of the progeny received cenh3 when crossed through the male and 25% when crossed through the female (Table 4).

TABLE 4

| | | | | | |
|---|---|---|---|---|---|
| Transmission of cenh3 through male and female crosses *. | | | | | |
| Cross | # seedlings | expected WT:het:hom | expected het frequency | observed WT.het:hom | observed het frequency |
| +/cenh3 ⊗ | 218 | 55:109:55 | 50% | 163:55:0 | 25.2% |
| +/cenh3 ♀ X B73 ♂ | 184 | 90:90 | 50% | 138:46:0 | 25.0% |
| B73 ♀ X +/cenh3 ♂ | 140 | 70:70 | 50% | 123:17:0 | 12.1% |

* WT indicates wild type, het indicates +/cenh3 heterozygote, hom indicates cenh3/cenh3 homozygote.

The reduction in transmission may be explained because sperm and eggs are carried within multicellular haploid gametophytes. Two haploid cell divisions precede the formation of spern and three haploid cell divisions precede the formation of an egg. Those gametophytes with the cenh3 allele must use CENH3 carried over from the sporophytic phase while it is naturally diluted at each cell cycle (Lermontova, et al., *Plant Cell* 18, 2443-2451 (2006)). Under this model, cenh3 sperm would have about % of the normal amount of CENH13 and an egg carrying cenh3 would have about % relative to the cenh3 heterozygous parent (FIG. 4B). Assuming no dosage compensation, those values would be reduced by an additional b relative to a nonnal homozygous wild type parent. As a result, sperm and eggs carrying cenh3 may have smaller centromeres.

To test whether+Icenh3 heterozygous mutants are able to induce haploids, cenh3 heterozygotes were crossed with tester lines in both directions. In the first test wild type and +/cenh3 plants were crossed to a line that is homozygous for a recessive glossY8 (gl8) mration on chromosome 5 that causes seedling leaves to have a shiny appearance (Xu, et al., *Plant Physiology* vol. 115 501-510 (1997)). It was observed that 0.5% of the progeny were glossy when +/cenh3 heterozygotes was crossed as male, and 5.0% of the progeny were haploid when +/cenh3 plants were crossed as female (Table 5).

TABLE 5

| | | | | | | |
|---|---|---|---|---|---|---|
| Haploid and aneuploid induction by +/cenh3 heterozygotes. | | | | | | |
| Cross | # seedlings | # glossy pants | # haploid | haploid ratio | # aneuploid | aneuploid ratio |
| gl8 ♀ X +/cenh3 ♂ | 597 | 3 | 3 | 0.5% | 0 | 0 |
| gl8 ♀ X WT ♂ | 826 | 0 | — | — | — | — |
| +/cenh3 ♀ X gl8 ♂ | 838 | 42 | 42 | 5.0% | 2 [1] | 0.2% |
| WT ♀ X gl8 ♂ | 1000 | 0 | — | — | — | — |
| +/cenh3 ♀ X gl1 ♂ | 844 | 75 | 44 | 5.2% | 28 | 3.3% |
| WT ♀ X gl1 ♂ | 1114 | 0 | — | — | — | — |

[1] The two aneuploid plants are non-glossy plants with stunted phenotypes.

Figure 2A:
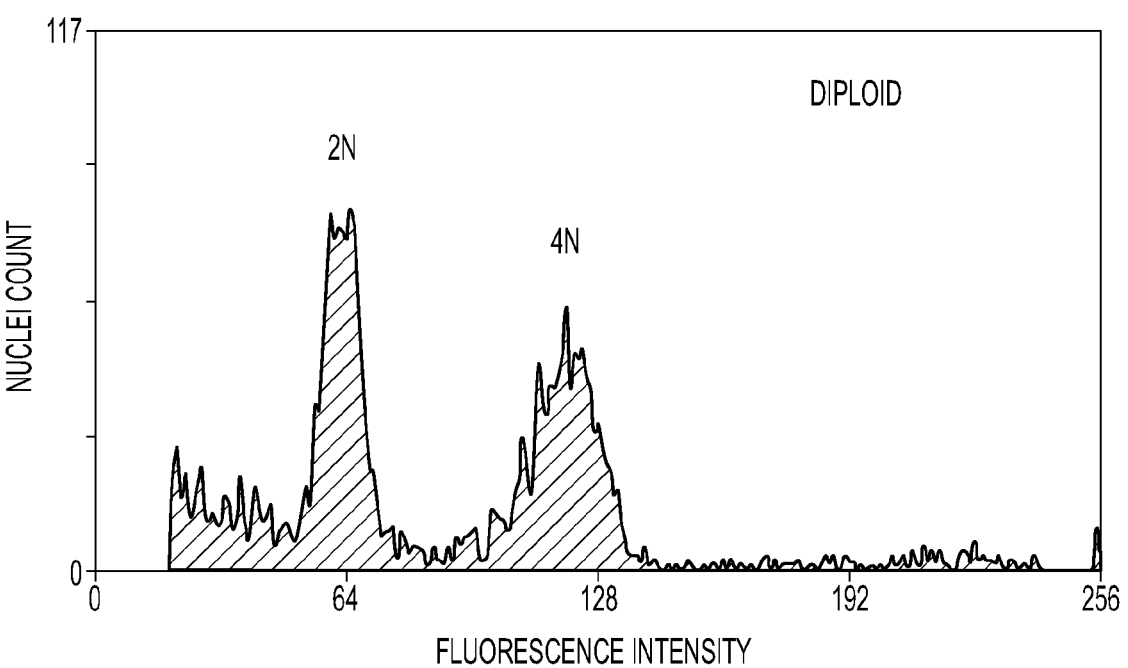
FIGS. 2A-2F illustrate the results of assays confirming that plants are haploid.
Figure 2B:
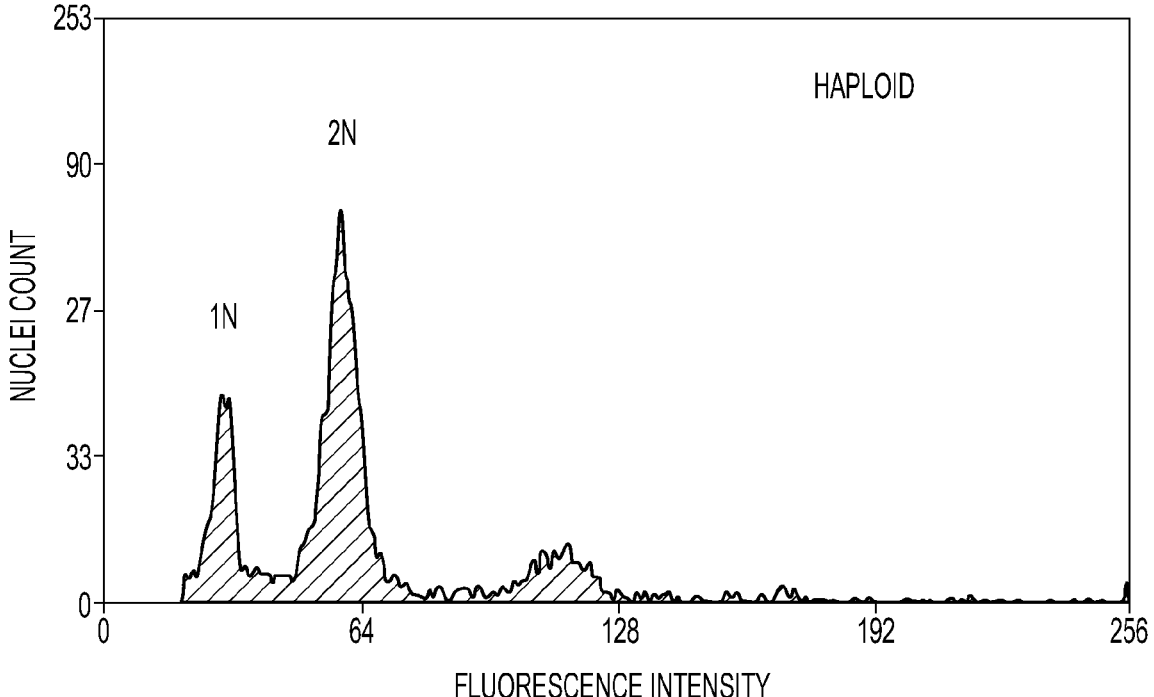
Figure 2C:
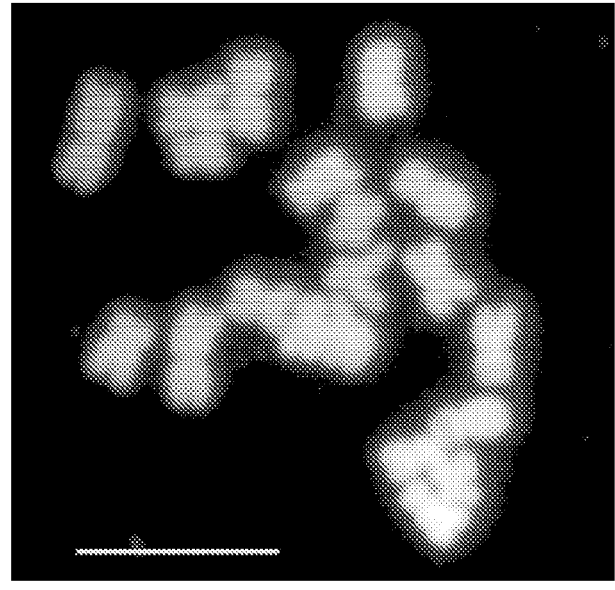
Figure 2D:
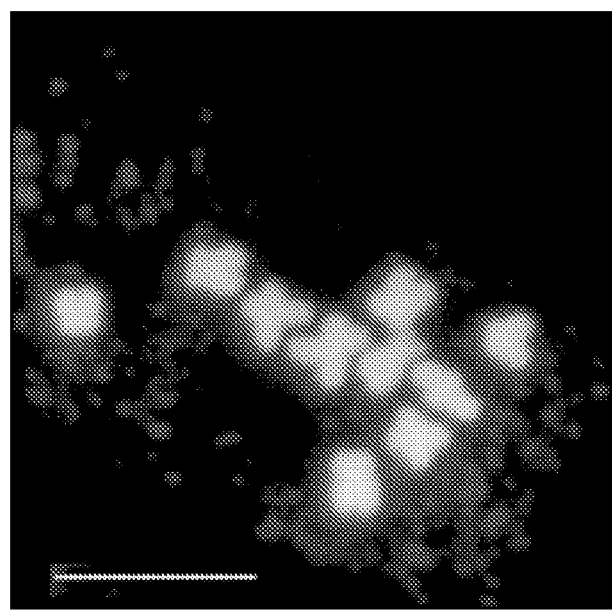
Figure 2E:
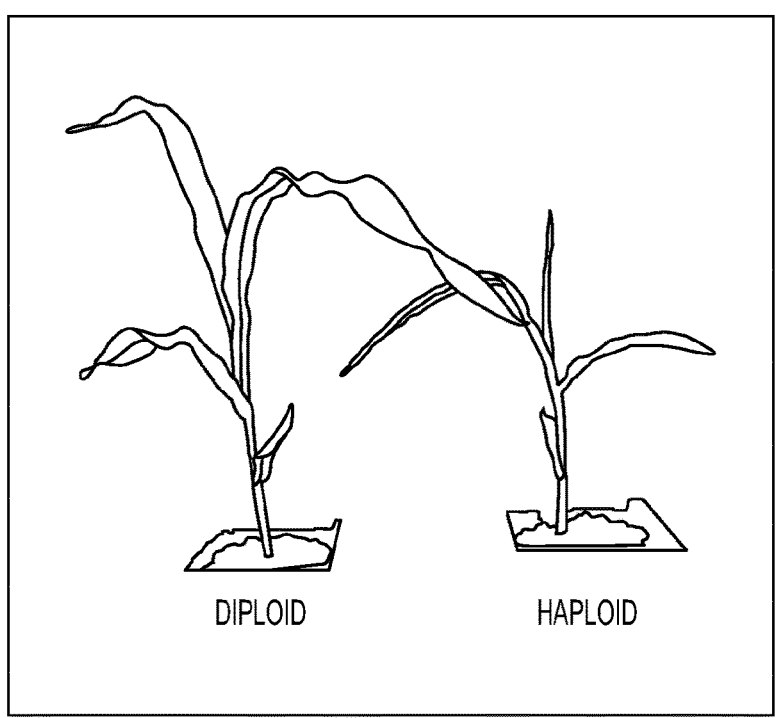
Figure 2F:
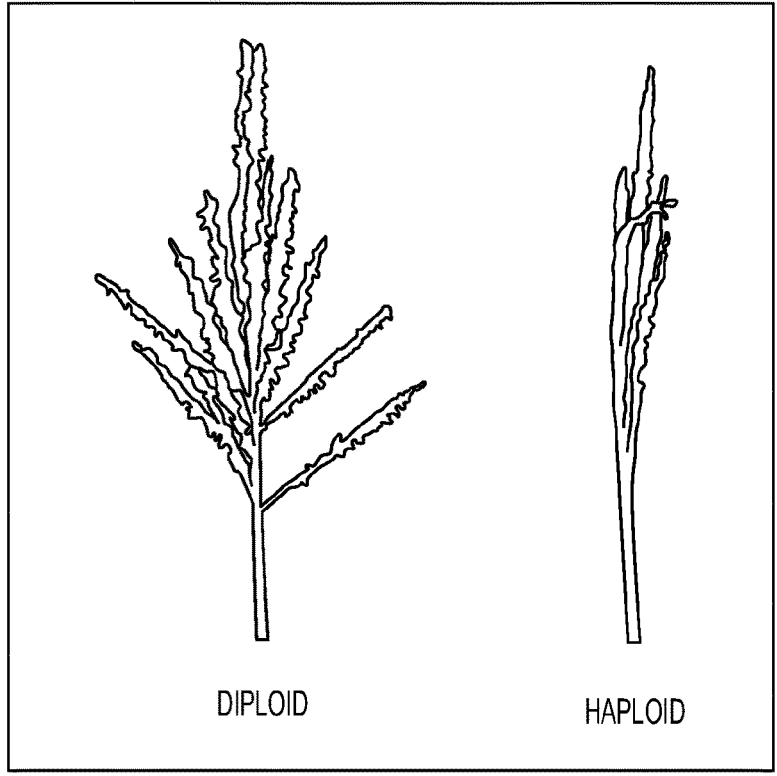
Figure 3A:
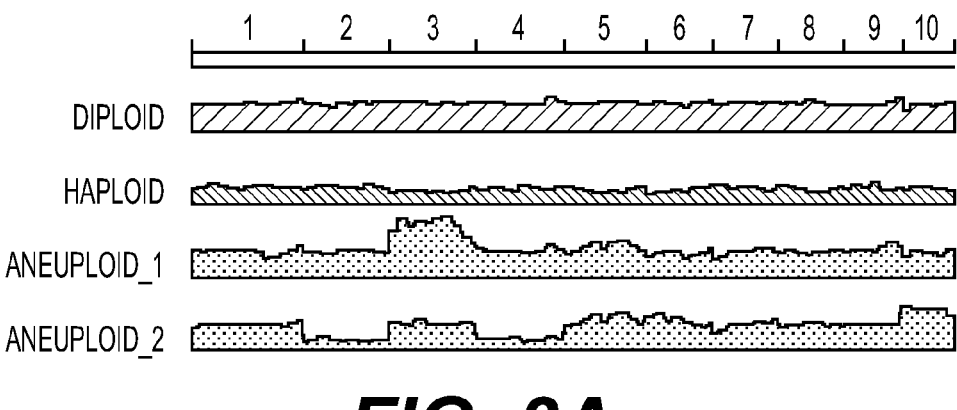
FIGS. 3A and 3B are plots illustrating the molecular karyotypes of aneuploids. For both panels, the chromosomes are shown end to end across the top.
Figure 3B:
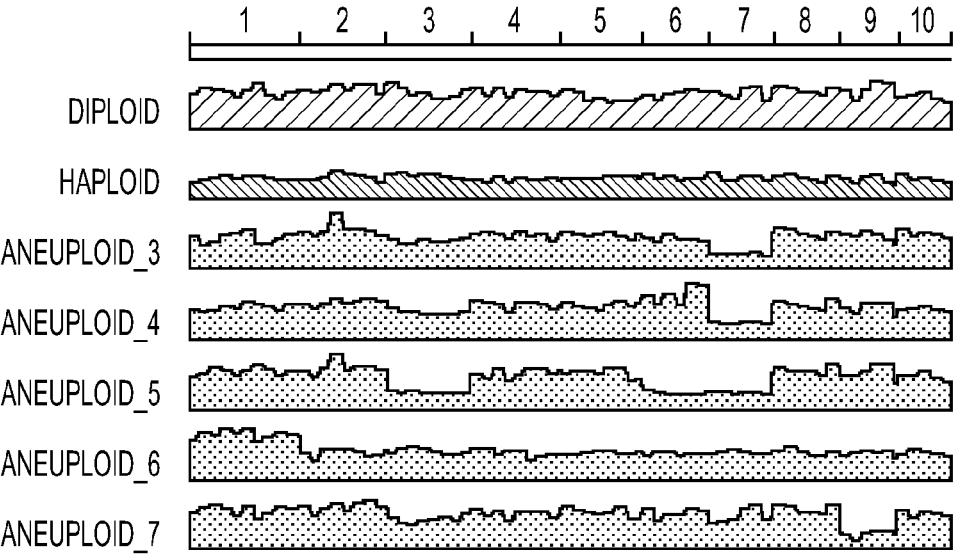

Flow cytometry analysis revealed that all of the glossy plants were haploids (FIG. 2A-2B), an interpretation that was confirmed by counting chromosomes in root tip cells of three plants (FIG. 2C-2D). When grown to maturity the haploid plants were short and sterile (Chase, *Bot. Rev.* 35, 117-168 (1969)) (FIG. 2E-2F). Also observed were two non-glossy plants with stunted phenotypes that were believed to be aneuploids. These two plants were skim sequenced along with six haploids. While the haploids showed uniform sequence coverage, the stunted plants did not; one was trisomic for chromosome 3, and the other was monosomic for chromosome 2 and 4 and trisomic for chromosome 10 (FIG. 3A-3B).

A second set of tests was carried out using glossyl (gl1), which has a similar phenotype but the mutation is on chromosome 7 (Sturaro, et al., *Plant Physiol.* 138, 478-489 (2005)). In these crosses the germination rate was also scored, which is an indirect measure of karyotypic abnormality commonly used to score the efficacy of Arabidopsis haploid inducers (Kuppu, et al., *PLoS Genet.* 11, e1005494 (2015), Ravi, et al., *Nature Communications* vol. 5 (2014), Maheshwari, et al., *PLoS Genet.* 11, e1004970 (2015)). In crosses where +/cenh3 heterozygotes were the female, 5.2% of the progeny showed the glossy phenotype and were haploid by flow cytometry measurements. Another 3.3% of the progeny showed the glossy phenotype but had a higher DNA content than expected for haploids, and were scored as aneuploids (Table 6).

TABLE 6

Results of individual crosses between +/cenh3 plants and the gl1 tester.

| cross [1] | seeds | seedlings | germination ratio | # glossy plants | # haploid | haploid ratio | # aneuploid | aneuploid ratio |
|---|---|---|---|---|---|---|---|---|
| NW222 | 192 | 147 | 76.6% | 13 | 7 | 4.8% | 6 | 4.1% |
| NW223 | 192 | 174 | 90.6% | 7 | 2 | 1.2% | 5 | 2.9% |
| NW224 | 192 | 157 | 81.8% | 19 | 14 | 8.9% | 5 | 3.2% |
| NW225 | 192 | 140 | 72.9% | 14 | 11 | 7.9% | 3 | 2.1% |
| NW227 | 180 | 117 | 65.0% | 10 [2] | 3 | 2.6% | 6 | 5.1% |
| NW228 | 165 | 109 | 66.1% | 12 [2] | 7 | 6.4% | 3 | 2.8% |
| | | | | | | | | |
| Total: | 1113 | 844 | 75.8% | 75 [2] | 44 | 5.2% | 28 | 3.3% |
| WT X gl1 | 1125 | 1114 | 99.0% | 0 | 0 | 0 | 0 | 0 |

[1] NW222, NW223, NW224, NW225, NW227, and NW228 are different ears from the cross +/cenh3 ♀ X gl1♂.

[2] unable to interpret the ploidy level in three glossy plants.

Different crosses differed considerably in the germination rate (65-91%), frequencies of haploids (1.2-8.9%) and aneuploids (2.1-5.1%) (Table 6). Sequence data from five aneuploid plants confirmed that all except one were missing chromosome 7, sometimes in conjunction with the loss of other chromosomes. One glossy plant that appeared to have two complete copies of chromosome 7 may have had a small interstitial deletion that was not detectable by skim sequencing (segmental aneuploids are common in Arabidopsis GFP-tailswap crosses (Tan, et al., Eife 4, (2015))). The results from the gl1 tests are more in line with what has been observed in Arabidopsis, where any given cross with GFP-tailswap generally yields haploids and aneuploids in similar proportions (Ravi and Chan, Nature 464, 615-618 (2010), Ravi, et al., Nature Communications vol. 5 (2014), Maheshwari, et al., PLoS Genet. 11, e1004970 (2015)).

If CENH3 dilution is the underlying mechanism for haploid induction, then only gametes carrying the cenh3 mutation from the +/cenh3 parent should induce haploids. Unfortunately it is not possible to score seedlings for the presence of the cenh3 allele because the genotne of the haploid inducer is lost. However, data from Arabidopsis GFP-tailswap crosses show that endosperm rarely displays complete uniparental genome elimination when the seedling is haploid (Ravi, et al., Nature Communications vol. 5 (2014)). If true in maize as well, the genotype of the endosperm could be used to determine the original genotype of the seedling. The remnant endosperm from a set of eleven haploid plants produced from a +/cenh3 X gl8 cross was genotyped. The results revealed that all eleven were heterozygous for the cenh3 allele, strongly supporting the interpretation that haploid induction is a result of the low CENH3 levels in cenh3 gametes.

One of the striking elements of centromere-mediated haploid induction is that it is effective in only a subset of progeny. In some individuals, all the chromosomes from the haploid inducer parent are lost, and in another much larger subset no chromosome loss occurs. The relatively small aneuploid class represents "partial haploid induction" events, where some chromosomes were lost but others survived. The fact that the gi8 crosses yielded more true haploids than the gi1 crosses may be related to the fact that the former were carried out in the summer while the latter were carried out in winter. It is also possible that the selection scheme played a role. Studies using the maize r-XI deletion line, which generates monosomics at high frequency, have demonstrated that some chromosomes are recovered as monosomics at higher frequency than others[28]. Monosomics for chromosome 5 (with gl8) are rarely recovered whereas monosomics for chromosome 7 (with gl1) are far more common (17 times more common (Weber, Use of Maize Monosomics for Gene Localization and Dosage Studies. in The Maize Handbook (eds. Freeling, M. & Walbot, V.) 350-358 (Springer New York, 1994))). Indeed, two of five sequenced aneuploids from gl1 crosses were monosomic for chromosome 7 only (Table 6). These data may indicate that the gl8 tester favors the recovery of haploids while the gl1 tester recovers a broader range of ploidies.

It is believed that all prior literature on centromere mediated haploid induction describes the complementation of a null allele with a variant of CENH3 or alleles that produce altered or partially deleted forms of CENH3 (Ravi and Chan, Nature 464, 615-618 (2010), Karimi-Ashtiyani, et al., Proc. Natl. Acad. Sci. U.S.A 112, 11211-11216 (2015), Kuppu, et al., Plant Biotechnol. J. (2020) doi:10.1111/pbi.13365, Maheshwari, et al., PLoS Genet. 11, e1004970 (2015), Ishii, et al., Annu. Rev. Plant Biol. 67, 421-438 (2016)). These data have served to sustain the original interpretation that haploid induction is caused by a competition between two structurally different forms of CENH3, and ultimate rejection of the altered centromneres by a surveillance mechanism for improper assembly (Ravi and Chan, Nature 464, 615-618 (2010), Britt and Kuppu, Front. Plant Sci. 7, 357 (2016), Kalinowska, et al., Theor. Appl. Genet. 132, 593-605 (2019), Kuppu, et al., Plant Biotechnol. J. (2020) doi:10.1111/pbi.13365, Maheshwari, et al., PLoS Genet. 11, e1004970 (2015), Copenhaver, & Preuss, Nat. Biotechnol. 28, 423-424 (2010)), compared to other possible mechanisms (Wang & Dawe, Molecular Plant vol. 11 398-406 (2018), Karimi-Ashtiyani, et al., Proc. Natl. Acad. Sci. U.S.A 112, 11211-11216 (2015), Ravi, et al., PLoS Genet. 7, e1002121 (2011), Wang, et al., Plant Methods 15, 42 (2019), Sanei, et al., Proc. Natl. Acad. Sci. U.S.A 108, E498-505 (2011), Tan, et al., Elife 4, (2015)).

In contrast, the data herein achieved high levels of haploid induction using a cenh3 mutation in the N-terminal tail that removes all sequence that interacts with DNA or other histones. Therefore, quantitative reductions in CENH3 alone can induce centromere-mediated haploid induction. The major advantage of the cenh3 null approach is that the plants are vigorous and the process is simple. Any line that is crossed to cenh3 becomes a haploid inducer. The ease of use should make it particularly versatile when combined with other technologies that are built upon haploids, such as synthetic apomixis (Marimuthu, et al., Science, 331(6019): 876 (2011), Wang, et al., aBIOTECH, 1:15-20(2020)), the transfer of engineered chromosomes from one line to another (Birchler, et al., Curren Opinion in Plant Biology, 19:76-80 (2014)), and genotype-independent gene editing (Kelliher, et al., Nat. Biotechnol. 37, 287-292 (2019)).

Example 2: Haploid Induction with Simultaneous
Gene Editing

Materials and Methods

A use of the cenh3 haploid inducer involves simultaneous haploid induction and gene editing. In an example of this use, the cenh3 null is first crossed to a line containing a CRISPR construct (expressing both Cas9 and a one or more guide RNAs). This hybrid line, with both cenh3 and CRISPR components, is then crossed as a female to a male wild type maize line. It is believed that upon fertilization, roughly 5% of the progeny will be haploid, and among these, approximately half will have received the CRISPR construct expressing Cas9 and guide RNA(s). CRISPR components are expressed in the early zygotic divisions and where can catalyze gene editing on the genome of the paternal genome. The genome of the female parent will be rapidly lost during haploid induction, removing the CRISPR components and leaving only the paternal genome, of which a fraction will have sustained gene editing.

To test haploid induction with simultaneous gene editing, experiments were designed to cross the cenh3 null to a CRISPR construct expressing Cas9 from the Ubiquitin promoter and eight guide RNAs targeting four genes that control plant development: fasciated ear-2 (fea2), fasciated ear-3 (fea3), compact plant-2 (ct2), and thick tassel dwarf-1 (td1). The CRISPR construct was first introduced by Agrobacterium-mediated transformation into an inbred called B104. The transgenic B104 line was then crossed to the heterozygous cenh3 null plant. From the progeny of this cross, plants with both the CRISPR construct and cenh3 were crossed to maize line homozygous for a recessive mutation called luteus-1 to identify haploids.

Results

Of a total of 192 plants, 7 proved to be haploids. A total of 40 diploid plants and all 7 haploid plants were genotyped (by amplicon Sanger sequencing) for edits at each guide RNA site. The overall editing frequency was low, yielding a total of five edits among the forty diploid plants. However, importantly, one of the haploid plants was edited at the fea2 gene. The edit in the haploid plant conferred a fasciated ear phenotype consistent with the known recessive phenotype of this mutant (Taguchi-Shiobara, et al., *Genes Dev.* 15: 2755-2766 (2001)). The editing frequency of 1/7 in haploids roughly matches the editing frequency of 5/40 in diploids, indicating, in this small early trial experiment, that editing is roughly as efficient in haploid and diploids.

Of further note is the fact that the single edit is of a non-standard type. While the edits in diploids were consistent with cleavage and repair by non-homologous end joining (NHEJ), the haploid plant contained an insertion flanked by a short region of homology on either side. This type of edit may indicate erroneous homology-directed repair (HDR) (Xue and Greene, *Trends in Genetics*, DOI: 10.1016/j.tig.2021.02.008. (2021)). These data provide reason to believe that HDR is active during the early zygotic divisions, and that cleavage and repair can occur during the brief time that both genomes are present, prior the loss of the chromosomes from the haploid inducer line. HDR is an important form of repair for many CRISPR applications involving replacement of promoters or genes with new sequences (Zhang et al., *Nat Plants*, 5: 778-794 (2019)).

Figure 5A:
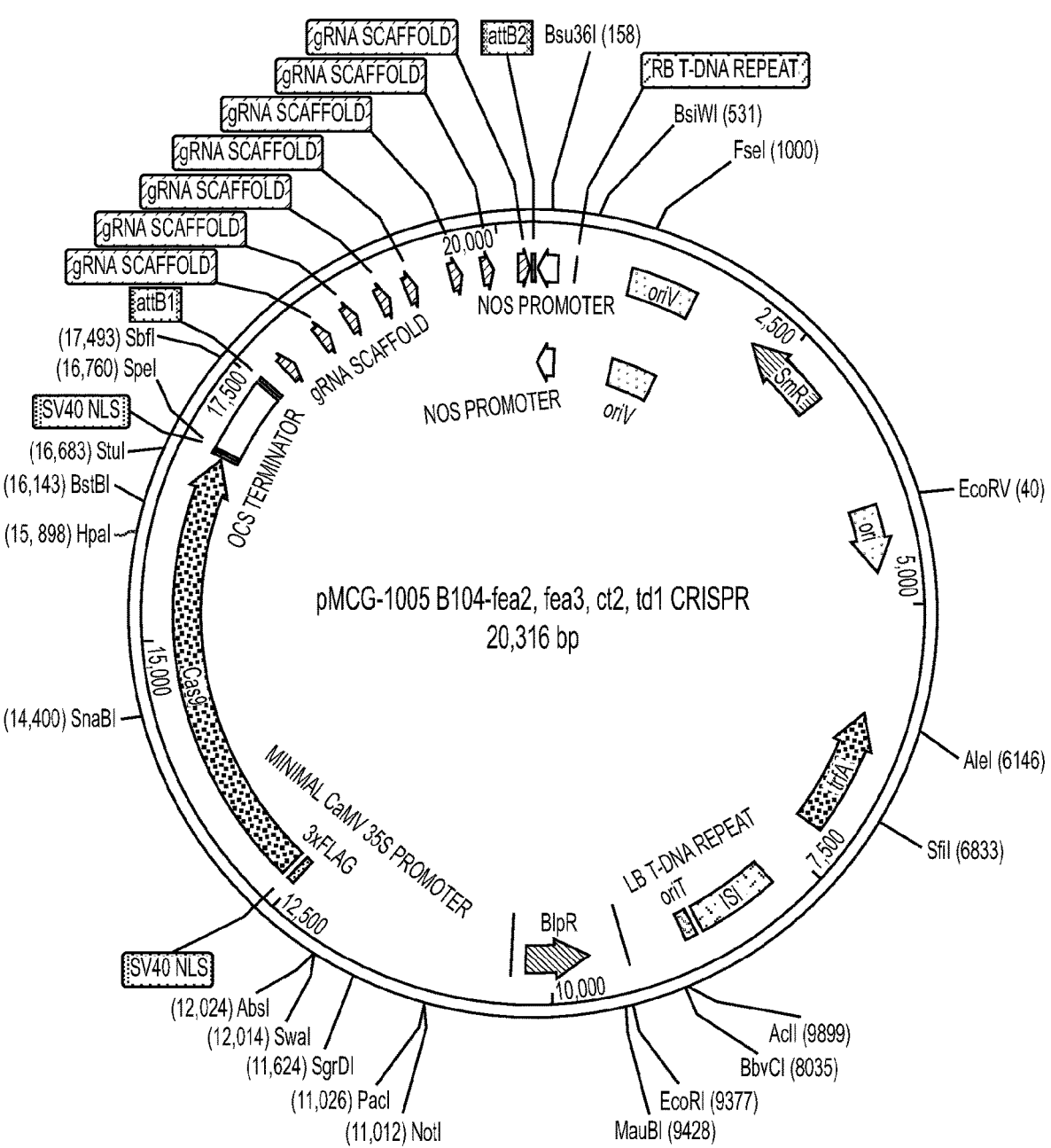
FIGS. 5A-5D illustrate Application of the cenh3 null in simultaneous haploid induction and gene editing.
Figure 5B:
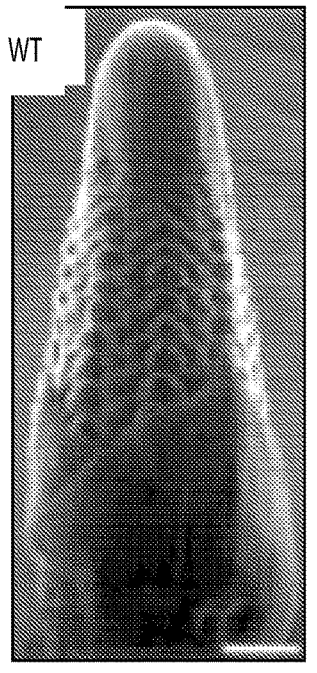
Figure 5C:
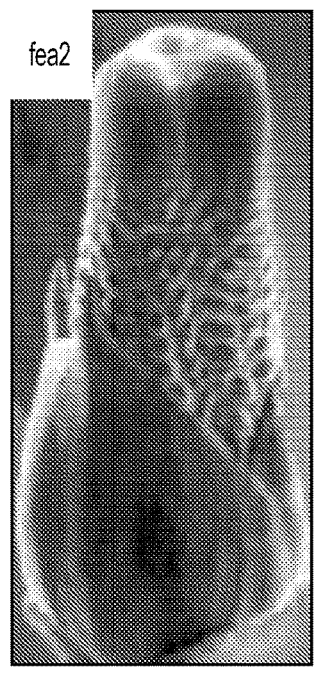
Figure 5D:
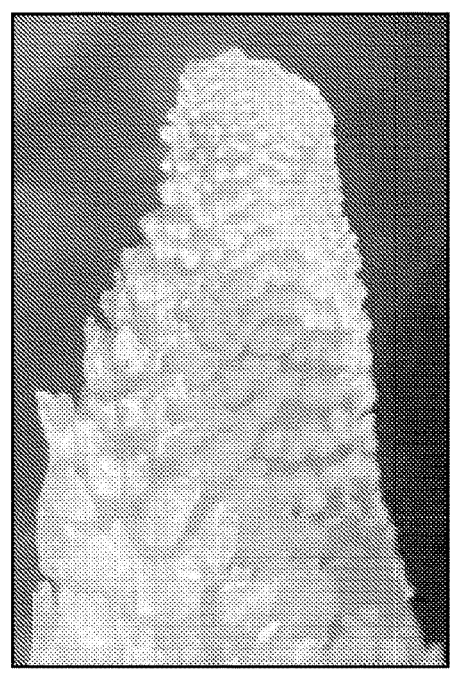

The results of these experiments are illustrated in FIGS. 5A-5D and Tables 7 and 8. FIG. 5A is a plasmid map of the CRISPR construct used for simultaneous haploid induction and gene editing. Construct components are indicated.

TABLE 7

Frequency of edits from diploid and haploid progeny of cenh3 heterozygous plant carrying Cas9 and eight gRNAs (SEQ ID NOS: 30-37, in descending order as they appear in the table).

| Gene: | gRNA | gRNA sequence | SEQ ID NO: | Haploid Edits | Diploid Edits |
|---|---|---|---|---|---|
| FEA3 | 1 | GCGCCCAGCTGTTCGACCTG | 30 | 0/7 | 0/40 |
| FEA3 | 2 | GCTCGTGGAGAACAACCTGA | 31 | 0/7 | 0/40 |
| FEA2 | 1 | GGAAGGCGAGAAGCGCTGCG | 32 | 0/7 | 1/40 |
| FEA2 | 2 | GTACGGCTGCGATACCGGCG | 33 | 1/7* | 2/40 |
| TD1 | 1 | GTCGCCAACTGCTATCTCCG | 34 | 0/7 | 0/39 |
| TD1 | 2 | GGATACTACAACCAGTACAG | 35 | 0/7 | 1/39 |
| CT2 | 1 | GTAAGGTGCTGGAGAATCG | 36 | 0/7 | 0/40 |
| CT2 | 2 | GCTTTGACGAGGCAGAGCTT | 37 | 0/7 | 1/40 |
| | | Total edits | | 1/7 | 5/40 |

TABLE 8

Illustration/Alignment of the Edits (SEQ ID NOS:38-47, in descending order as they appear in the table)

| Gene: | SEQ ID NO: | gRNA sequence |
|---|---|---|
| FEA2 WT Guide 1 | 38 | CGC*GGAAGGCGAGAAGCGCTGCG*CGGTCGGTGGAGGCAGGGACTGCAGGTTGGGTCGCCGACGCCAGGAC |

TABLE 8-continued

Illustration/Alignment of the Edits (SEQ ID NOS:38-47, in descending
order as they appear in the table)

| Gene: | SEQ ID NO: | gRNA sequence |
|---|---|---|
| FEA2$^{CR1}$ diploid | 39 | *CGCGGAAGGCGAGAAG- - -TGCGCGGTCGGTGGAGGCAGGGACTGCAGGTTGGGTCGCCG* ACGCCAGGAC |
| FEA2 WT Guide 2 | 40 | TCCG*TACGGCTGCGATACCGGC*GGGGATCTCGCCGGAGAAGCGGTTGTGGGAGAGGTCGA |
| FEA2$^{CR2}$ diploid | 41 | TCCG*TACGGCTGCGATAC- -GCG*GGGGATCTCGCCGGAGAAGCGGTTGTGGGAGAGGTCGA |
| FEA2$^{CR3}$ diploid | 42 | TCCG*TACGGCTGCGATACC-GCG*GGGGATCTCGCCGGAGAAGCGGTTG*I*GGGAGAGGTCGA |
| FEA2$^{CR4}$ haploid | 43 | TCCG*TACGGCTGCGATACCGGCG***GGGATCTcgccggagaagcggttgtgggagaggtcga ggaggaggagagcggagttgtcggggtcggcgacgatccgcggcgggacgg*CGCCGGAGA*** AGCGGI TGTGGGAGAGGTCGAGGAGGAGGAGAGCGGAGTTGTCGGGGTCGG<u>CGACGATCC</u> <u>GCGGCGGGACGGCGCCGGAGA</u>TGGCGTTGCGGGAGAGATCAAGGGCAGCGAGGCGCGCGG GGAAGGAGAGACGCGGGGAGAGCGGG |
| TD1 WT Guide 2 | 44 | GTC*GGATACTACAACCAGTACAG*CGGCGGGGTCCCGCGCGAGTTCGGCGCGCTCCAGTCGC |
| TD1$^{CR1}$ diploid | 45 | GTC*GGATACTACAACCAGT-CAGC*GGCGGGGTCCCGCGCGAGTTCGGCGCGCTCCAGTCGC |
| CT2 WT Guide 2 | 46 | CT*GGCTTGACGAGGCAGAGCTT*AGGAGCTACACATCAGTCATCCATGCTAATGTGTATCAG |
| CT2$^{CR1}$ diploid | 47 | CT*GGCTTGACGAGGCAGA-CTT*AGGAGCTACACATCAGTCATCCATGCTAATGTGTATCAG |

The edits in diploid plants are within the gRNA regions, consistent with cleavage and repair by NHEJ. The edit in the haploid plant is an 81 bp insertion suggestive of repair by erroneous HDR, presumably mediated by the flanking region of microhomology. Annotations indicate the following features: guide RNA target regions, PAM sites; deleted bases (dashes); duplicated region; homology flanking duplication. WT=wild type.

A very small experiment with a different construct (directed to ZmGB1) yielded no detectable edits in haploids and only a few in diploids.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A diploid monocot haploid inducer plant heterozygous for centromeric histone 3 (CenH3) comprising diploid plant cells comprising only two CenH3 alleles, wherein one allele encodes wildtype CENH3 protein and the other allele is a null allele, and wherein the diploid plant cells express an exogenous CRISPR-based site-directed nuclease and a guide RNA, and the plant's genome further comprises a donor nucleic acid sequence to be introduced by recombination at a cleavage site induced by the nuclease.

2. The monocot plant of claim 1, wherein the sperm or eggs of the plant have less CENH3 than a CENH3 homozygous wildtype plant's sperm or eggs.

3. The monocot plant of claim 1, wherein the plant is a diploid species of maize, wheat, rice, sorghum, oats, pearl millet, finger millet, foxtail millet, banana, bamboo, Miscanthus, asparagus, onion, garlic, chives, or yam.

4. The monocot plant of claim 1, wherein the CRISPR-based nuclease is selected from Cas9 nuclease, Cpf1 nuclease, dCas9-FokI, dCpf1-FokI, chimeric Cas9-cytidine deaminase, chimeric Cas9-adenine deaminase, chimeric FEN1-FokI, nickase Cas9 (nCas9), chimeric dCas9 non-FokI nuclease, dCpf1 non-FokI nuclease, chimeric Cpf1-cytidine deaminase, and Cpf1-adenine deaminase.

5. The monocot plant of claim 1, wherein the plant's genome comprises a heterologous nucleic acid construct encoding the gRNA.

6. An egg cell formed by the plant of claim 1, the egg cell lacking the allele encoding wildtype CENH3 protein and comprising no more than about 12.5% wildtype CENH3 protein relative to a corresponding egg cell formed by a CenH3 homozygous plant.

7. A sperm cell formed by the plant of claim 1, the sperm cell lacking the allele encoding wildtype CENH3 protein and comprising no more than about 25% wildtype CENH3 protein relative to a corresponding sperm cell formed by a CenH3 homozygous plant.

8. A method of inducing formation of a target haploid monocot plant comprising pollinating a parent monocot target plant with pollen from a diploid monocot haploid inducer plant and selecting at least one haploid progeny produced by the pollination, wherein the diploid monocot haploid inducer plant is heterozygous for centromeric histone 3 (CenH3) comprising diploid plant cells comprising only two CenH3 alleles, wherein one allele encodes wildtype CENH3 protein and the other allele is a null allele.

9. A method of inducing formation of a target haploid monocot plant comprising pollinating a diploid monocot haploid inducer plant with pollen from a parent monocot target plant and selecting at least one haploid progeny produced by the pollination, wherein the diploid monocot haploid inducer plant is heterozygous for centromeric histone 3 (CenH3) comprising diploid plant cells comprising only two CenH3 alleles, wherein one allele encodes wildtype CENH3 protein and the other allele is a null allele.

10. The method of claim 8, wherein the monocot haploid inducer plant comprises an exogenous site-directed nuclease expressed by cells of the monocot haploid inducer plant, and wherein the haploid progeny comprises the genome of the monocot target plant but not the monocot haploid inducer plant, and the genome of the haploid progeny has been modified by the site directed nuclease and optionally at least one guide RNA delivered by the monocot haploid inducer plant.

11. The method of claim 8, further comprising chromosome doubling of the selected haploid progeny.

12. The method of claim 9, wherein the monocot haploid inducer plant comprises an exogenous site-directed nuclease expressed by cells of the monocot haploid inducer plant, and wherein the haploid progeny comprises the genome of the monocot target plant but not the monocot haploid inducer plant, and the genome of the haploid progeny has been modified by the site directed nuclease and optionally at least one guide RNA delivered by the monocot haploid inducer plant.

13. The method of claim 9, further comprising chromosome doubling of the selected haploid progeny.

14. The method of claim 10, wherein the monocot haploid inducer plant comprises the at least one guide RNA.

15. The method of claim 12, wherein the monocot haploid inducer plant comprises the at least one guide RNA.

16. The method of claim 8, wherein the monocot haploid inducer plant is a diploid species of maize, wheat, rice, sorghum, oats, pearl millet, finger millet, foxtail millet, banana, bamboo, Miscanthus, asparagus, onion, garlic, chives, or yam.

17. The method of claim 8, wherein the monocot haploid inducer plant is maize.

18. The method of claim 9, wherein the monocot haploid inducer plant is a diploid species of maize, wheat, rice, sorghum, oats, pearl millet, finger millet, foxtail millet, banana, bamboo, Miscanthus, asparagus, onion, garlic, chives, or yam.

19. The method of claim 9, wherein the monocot haploid inducer plant is maize.

* * * * *

SEQUENCE LISTING

<160> NUMBER OF SEQ ID NOS: 47

<210> SEQ ID NO 1
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 1
tcccgcagcg ctacagtccc                                                    20

<210> SEQ ID NO 2
<211> LENGTH: 23
<212> TYPE: DNA
<213> ORGANISM: Artificial Sequence
<220> FEATURE:
<223> OTHER INFORMATION: synthetic polynucleotide -continued

```
<400> SEQUENCE: 2
ccaggtacgg tcgccctgcg cga                                            23

<210> SEQ ID NO 3
<211> LENGTH: 42
<212> TYPE: DNA
<213> ORGANISM: Artificial Sequence
<220> FEATURE:
<223> OTHER INFORMATION: synthetic polynucleotide

<400> SEQUENCE: 3
atggatgaac tatacaaggg cggaggcggt ggaggcgtcg ac                       42

<210> SEQ ID NO 4
<211> LENGTH: 21
<212> TYPE: DNA
<213> ORGANISM: Artificial Sequence
<220> FEATURE:
<223> OTHER INFORMATION: synthetic polynucleotide

<400> SEQUENCE: 4
tgcaagatga gggcgaatgt g                                              21

<210> SEQ ID NO 5
<211> LENGTH: 21
<212> TYPE: DNA
<213> ORGANISM: Artificial Sequence
<220> FEATURE:
<223> OTHER INFORMATION: synthetic polynucleotide

<400> SEQUENCE: 5
tacttcctga tctcccgcag c                                              21

<210> SEQ ID NO 6
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 6
ggctgctctt acttgcttgc                                                20

<210> SEQ ID NO 7
<211> LENGTH: 23
<212> TYPE: DNA
<213> ORGANISM: Artificial Sequence
<220> FEATURE:
<223> OTHER INFORMATION: synthetic polynucleotide

<400> SEQUENCE: 7
cgctctactt tcccgtttgt tac                                            23

<210> SEQ ID NO 8
<211> LENGTH: 24
<212> TYPE: DNA
<213> ORGANISM: Artificial Sequence
<220> FEATURE:
<223> OTHER INFORMATION: synthetic polynucleotide

<400> SEQUENCE: 8
tacttcctga tctcgcgcag ggcg                                           24

<210> SEQ ID NO 9
```

<211> LENGTH: 24
<212> TYPE: DNA
<213> ORGANISM: Artificial Sequence
<220> FEATURE:
<223> OTHER INFORMATION: synthetic polynucleotide

<400> SEQUENCE: 9
acgagaagta cccgacaatc tacc                                                          24

<210> SEQ ID NO 10
<211> LENGTH: 22
<212> TYPE: DNA
<213> ORGANISM: Artificial Sequence
<220> FEATURE:
<223> OTHER INFORMATION: synthetic polynucleotide

<400> SEQUENCE: 10
tgatttgaag ttcggcgtca gg                                                            22

<210> SEQ ID NO 11
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 11
cgctcgaact ggagcttctt                                                               20

<210> SEQ ID NO 12
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 12
aggttggcag gtagccgtta                                                               20

<210> SEQ ID NO 13
<211> LENGTH: 21
<212> TYPE: DNA
<213> ORGANISM: Artificial Sequence
<220> FEATURE:
<223> OTHER INFORMATION: synthetic polynucleotide

<400> SEQUENCE: 13
gcctctattt cgtcgaatcc g                                                             21

<210> SEQ ID NO 14
<211> LENGTH: 21
<212> TYPE: DNA
<213> ORGANISM: Artificial Sequence
<220> FEATURE:
<223> OTHER INFORMATION: synthetic polynucleotide

<400> SEQUENCE: 14
gcctccattt cgtcgaatcc c                                                             21

<210> SEQ ID NO 15
<211> LENGTH: 13
<212> TYPE: DNA
<213> ORGANISM: Artificial Sequence
<220> FEATURE:
<223> OTHER INFORMATION: synthetic polynucleotide

<400> SEQUENCE: 15

-continued agatcggaag agc                                                              13

<210> SEQ ID NO 16
<211> LENGTH: 23
<212> TYPE: DNA
<213> ORGANISM: Artificial Sequence
<220> FEATURE:
<223> OTHER INFORMATION: synthetic polynucleotide

<400> SEQUENCE: 16
ccagggactg tagcgctgcg gga                                                   23

<210> SEQ ID NO 17
<211> LENGTH: 23
<212> TYPE: DNA
<213> ORGANISM: Artificial Sequence
<220> FEATURE:
<223> OTHER INFORMATION: synthetic polynucleotide

<400> SEQUENCE: 17
tcccgcagcg ctacagtccc tgg                                                   23

<210> SEQ ID NO 18
<211> LENGTH: 35
<212> TYPE: DNA
<213> ORGANISM: Artificial Sequence
<220> FEATURE:
<223> OTHER INFORMATION: synthetic polynucleotide

<400> SEQUENCE: 18
gccaccgctg gcggccaggg actgtagcgc tgcgg                                      35

<210> SEQ ID NO 19
<211> LENGTH: 34
<212> TYPE: DNA
<213> ORGANISM: Artificial Sequence
<220> FEATURE:
<223> OTHER INFORMATION: synthetic polynucleotide

<400> SEQUENCE: 19
gccaccgctg gcggccaggg ctgtagcgct gcgg                                       34

<210> SEQ ID NO 20
<211> LENGTH: 157
<212> TYPE: PRT
<213> ORGANISM: Zea mays

<400> SEQUENCE: 20

Met Ala Arg Thr Lys His Gln Ala Val Arg Lys Thr Ala Glu Lys Pro
1               5                   10                  15

Lys Lys Lys Leu Gln Phe Glu Arg Ser Gly Gly Ala Ser Thr Ser Ala
                20                  25                  30

Thr Pro Glu Arg Ala Ala Gly Thr Gly Gly Arg Ala Ala Ser Gly Gly
            35                  40                  45

Asp Ser Val Lys Lys Thr Lys Pro Arg His Arg Trp Arg Pro Gly Thr
        50                  55                  60

Val Ala Leu Arg Glu Ile Arg Lys Tyr Gln Lys Ser Thr Glu Pro Leu
65                  70                  75                  80

Ile Pro Phe Ala Pro Phe Val Arg Val Val Arg Glu Leu Thr Asn Phe
                85                  90                  95

Val Thr Asn Gly Lys Val Glu Arg Tyr Thr Ala Glu Ala Leu Leu Ala
            100                 105                 110

```
Leu Gln Glu Ala Ala Glu Phe His Leu Ile Glu Leu Phe Glu Met Ala
        115                 120                 125

Asn Leu Cys Ala Ile His Ala Lys Arg Val Thr Ile Met Gln Lys Asp
    130                 135                 140

Ile Gln Leu Ala Arg Arg Ile Gly Gly Arg Arg Trp Ala
145                 150                 155
```

```
<210> SEQ ID NO 21
<211> LENGTH: 1145
<212> TYPE: DNA
<213> ORGANISM: Zea mays

<400> SEQUENCE: 21
ctcccgtccc gagagttctg aatcgaaacc gtcggccacg agagcagtgc gaggcgccca      60
ccgcgatggc tcgaaccaag caccaggccg tgaggaagac ggcggagaag cccaagaaga     120
agctccagtt cgagcgctca ggtggtgcga gtacctcggc gacgccggaa agggctgctg     180
ggaccggggg aagagcggcg tctggaggtg actcagttaa gaagacgaaa ccacgccacc     240
gctggcggcc agggactgta gcgctgcggg agatcaggaa gtaccagaag tccactgaac     300
cgctcatccc ctttgcgcct ttcgtccgtg tggtgaggga gttaaccaat ttcgtaacaa     360
acgggaaagt agagcgctat accgcagaag ccctccttgc gctgcaagag gcagcagaat     420
tccacttgat agaactgttt gaaatggcga atctgtgtgc catccatgcc aagcgtgtca     480
caatcatgca aaaggacata caacttgcaa ggcgtatcgg aggaaggcgt tgggcatgat     540
atataatatc cattctgatt gcatcattct tgtgaatttg tttgtaggag ctagacatta     600
gtgttgttga atgctgcatg gttcctaatc cttttcgcag tctaacatct gtggagttag     660
tatgttacat ggcaacagct gaacatctgt ggactataac tatatggcaa cagccgaaga     720
ttgtgtctgt gggataactg gttgtttttgg ttgctcttca gtagtttgtt tgcttcaggt     780
aaccatgctg cgaactatga tgtttttcatt ctcggttttgc ttcagctaac cgagatcgat     840
tcagtctgca gtatatggac tatggagtaa actgcatgct gaaacccgaa ccactgctga     900
aacggcagtt gccaggatag caggaggggcc ctttatgcac agtggaattg agtagagaac     960
tgagtaaacc atggttcttt ctccttttga actggaacac aaacacagtt ggatcttgtt    1020
tctcttctta ggccattgtc atcgtgtttc ttaggggtgt aaatggtatc tgtccgtatt    1080
cgaatttgat ctatctaaca aggctgaaat ccgaaaaaaa aaaaaaaaaa aaaaaaaaaa    1140
aaaaa                                                                1145
```

```
<210> SEQ ID NO 22
<211> LENGTH: 164
<212> TYPE: PRT
<213> ORGANISM: Oryza sativa

<400> SEQUENCE: 22

Met Ala Arg Thr Lys His Pro Ala Val Arg Lys Ser Lys Ala Glu Pro
1               5                   10                  15

Lys Lys Lys Leu Gln Phe Glu Arg Ser Pro Arg Pro Ser Lys Ala Gln
            20                  25                  30

Arg Ala Gly Gly Gly Thr Gly Thr Ser Ala Thr Thr Arg Ser Ala Ala
        35                  40                  45

Gly Thr Ser Ala Ser Gly Thr Pro Arg Gln Gln Thr Lys Gln Arg Lys
    50                  55                  60

Pro His Arg Phe Arg Pro Gly Thr Val Ala Leu Arg Glu Ile Arg Lys
```

-continued

```
65              70              75              80

Phe Gln Lys Thr Thr Glu Leu Leu Ile Pro Phe Ala Pro Phe Ser Arg
                85              90              95

Leu Val Arg Glu Ile Thr Asp Phe Tyr Ser Lys Asp Val Ser Arg Trp
            100             105             110

Thr Leu Glu Ala Leu Leu Ala Leu Gln Glu Ala Ala Glu Tyr His Leu
        115             120             125

Val Asp Ile Phe Glu Val Ser Asn Leu Cys Ala Ile His Ala Lys Arg
    130             135             140

Val Thr Ile Met Gln Lys Asp Met Gln Leu Ala Arg Arg Ile Gly Gly
145             150             155             160

Arg Arg Pro Trp

<210> SEQ ID NO 23
<211> LENGTH: 828
<212> TYPE: DNA
<213> ORGANISM: Oryza sativa

<400> SEQUENCE: 23
acgccgcttc agtttgaaaa cccaccgcca cgtcgccgcc gccgccgccg ccgccgccga      60
cgccgagatg gctcgcacga agcacccggc ggtgaggaag tcgaaggcgg agcccaagaa     120
gaagctccag ttcgaacgct ccctcggcc gtcgaaggcg cagcgcgctg gtggcggcac     180
gggtacctcg gcgaccacga ggagcgcggc tggaacatcg gcttcaggga cgcctaggca     240
gcaaacgaag cagaggaagc cacaccgctt ccgtccaggc acagtggcac tgcgggagat     300
caggaaattt cagaaaacca ccgaactgct gatcccgttt gcaccatttt ctcggctggt     360
cagggagatc actgatttct attcaaagga tgtgtcacgg tggacccttg aagctctcct     420
tgcattgcaa gaggcagcag aataccactt agtggacata tttgaagtgt caaatctctg     480
cgccatccat gctaagcgtg ttaccatcat gcaaaaggac atgcaacttg ccaggcgtat     540
cggtgggcgg aggccatggt gaaaatttgt ttgcgagcca tgcagcatga tggacaagga     600
gcaacatgtg tcgttgatta acattttaga aagtagtgta gatgtatctt cacataggga     660
tcaacttacc cttcgttccc attctaattc agttgatgtt agtatttacc ttttgctcca     720
tttggattgg tcgaattcag gatttcatca aacagtcgat tgtgaaatgt gaaccaggaa     780
ttgttgtgtt gattgcaata atgggttcct ctcaaaaaaa aaaaaaaa                  828

<210> SEQ ID NO 24
<211> LENGTH: 163
<212> TYPE: PRT
<213> ORGANISM: Triticum aestivum

<400> SEQUENCE: 24

Met Ala Arg Thr Lys His Pro Ala Val Arg Lys Thr Lys Ala Pro Pro
1               5               10              15

Lys Lys Gln Leu Gly Pro Arg Pro Ala Gln Arg Gln Glu Thr Asp
            20              25              30

Gly Ala Gly Thr Ser Ala Thr Pro Arg Arg Ala Gly Arg Ala Ala Ala
        35              40              45

Pro Gly Gly Ala Gln Gly Ala Thr Gly Gln Pro Lys Gln Arg Lys Pro
    50              55              60

His Arg Phe Arg Pro Gly Thr Val Ala Leu Arg Glu Ile Arg Arg Tyr
65              70              75              80

Gln Lys Ser Val Asp Phe Leu Ile Pro Phe Ala Pro Phe Val Arg Leu
```

-continued

```
                    85              90              95
Ile Lys Glu Val Thr Asp Phe Phe Cys Pro Glu Ile Ser Arg Trp Thr
                100             105             110

Pro Gln Ala Leu Val Ala Ile Gln Glu Ala Ala Glu Tyr His Leu Val
            115             120             125

Asp Val Phe Glu Arg Ala Asn His Cys Ala Ile His Ala Lys Arg Val
            130             135             140

Thr Val Met Gln Lys Asp Ile Gln Leu Ala Arg Arg Ile Gly Gly Arg
145             150             155             160

Arg Leu Trp
```

```
<210> SEQ ID NO 25
<211> LENGTH: 492
<212> TYPE: DNA
<213> ORGANISM: Triticum aestivum

<400> SEQUENCE: 25
atggcccgca ccaagcaccc ggccgtcagg aagaccaagg cgccgcccaa gaagcagctc      60
gggccccgcc ccgcgcagcg gcggcaggag acagatggcg cgggcacgtc ggcgacaccg     120
aggcgagccg ggcgggcggc ggccccaggg ggggctcaag gggcaactgg gcaacccaag     180
cagaggaaac cacaccggtt caggccaggc acggtggcac tgcgggagat caggaggtat     240
cagaagtcgg tcgactttct catcccgttt gcaccatttg tccgtctgat caaggaggtc     300
accgacttct tctgtcctga aatcagccgc tggactcccc aagcgctcgt cgcgattcaa     360
gaggctgcag agtatcacct cgtcgacgta tttgaaaggg caaatcactg tgccatccat     420
gcaaagcgtg ttaccgtcat gcaaaaggac atacagcttg caaggcgtat cggcgggagg     480
aggctttggt ga                                                          492
```

```
<210> SEQ ID NO 26
<211> LENGTH: 139
<212> TYPE: PRT
<213> ORGANISM: Hordeum vulgare

<400> SEQUENCE: 26

Met Ala Arg Thr Lys Lys Thr Val Ala Ala Lys Glu Lys Arg Pro Pro
1               5               10              15

Cys Ser Lys Ser Glu Pro Gln Ser Gln Pro Lys Lys Lys Glu Lys Arg
            20              25              30

Ala Tyr Arg Phe Arg Pro Gly Thr Val Ala Leu Arg Glu Ile Arg Lys
            35              40              45

Tyr Arg Lys Ser Thr Asn Met Leu Ile Pro Phe Ala Pro Phe Val Arg
        50              55              60

Leu Val Arg Asp Ile Ala Asp Asn Leu Thr Pro Leu Ser Asn Lys Lys
65              70              75              80

Glu Ser Lys Pro Thr Pro Trp Thr Pro Leu Ala Leu Leu Ser Leu Gln
                85              90              95

Glu Ser Ala Glu Tyr His Leu Val Asp Leu Phe Gly Lys Ala Asn Leu
            100             105             110

Cys Ala Ile His Ser His Arg Val Thr Ile Met Leu Lys Asp Met Gln
        115             120             125

Leu Ala Arg Arg Ile Gly Thr Arg Ser Leu Trp
    130             135
```

```
<210> SEQ ID NO 27
```

```
<211> LENGTH: 768
<212> TYPE: DNA
<213> ORGANISM: Hordeum vulgare

<400> SEQUENCE: 27
gaacgaactc tatctctctc tctgcctgct ttccccacct gcgatggctc gcacgaagaa       60
aacggtggcg gcgaaggaga agcgcccccc ttgctccaag tcggagccgc agtcgcagcc      120
gaagaagaag gagaagcggg cgtaccggtt ccggccgggc acggtggcgc tgcgggagat      180
ccggaagtac cgcaagtcca ccaatatgct catccccttt gcgcccttcg tccgcctggt      240
cagggacatc gccgacaact tgacgccatt gtcgaacaag aaggagagca agccgacgcc      300
atggactcct ctcgcgctcc tctcgttgca agagtctgca gagtatcact tggtcgatct      360
atttggaaag gcaaatctgt gtgccattca ttcgcaccgt gttaccatca tgctaaagga      420
catgcagctt gcgaggcgta tcgggacgag aagcctttgg tgatactaat ggaggatgtt      480
ttaggcatcg tagggagcaa acactggtga tgctaatggt agatgttttt tgtatgagtg      540
caatgcgaag gagctgatgg tagtgatcca atatgtttgt gagtgtatca ttaggaagta      600
atgtaggtgt gttttcatct aggtagcatg tcttcgaagt tgatccggtt ggttgcatgg      660
ctgggatcat ctgacttgtc ggcttttgct ccatttgaat tgatctaatt cggacagagt      720
ttctgcaaat gatccaataa tatgggttgc caaaaaaaaa aaaaaaat                    768

<210> SEQ ID NO 28
<211> LENGTH: 167
<212> TYPE: PRT
<213> ORGANISM: Musa acuminata

<400> SEQUENCE: 28

Met Ala Arg Thr Lys His Leu Ser Asn Arg Ser Ser Ser Arg Pro Arg
1               5                   10                  15

Lys Arg Phe His Phe Gly Arg Ser Pro Gly Gln Arg Thr Pro Ala Asp
            20                  25                  30

Ala Asn Arg Pro Ala Thr Pro Ser Gly Ala Thr Pro Arg Thr Thr Ala
        35                  40                  45

Thr Arg Ser Arg Asp Thr Pro Gln Gly Ala Pro Ser Gln Ser Lys Gln
    50                  55                  60

Gln Pro Arg Arg Arg Arg Phe Arg Pro Gly Val Val Ala Leu Arg Glu
65                  70                  75                  80

Ile Arg Asn Leu Gln Lys Thr Trp Asn Leu Leu Ile Pro Phe Ala Pro
                85                  90                  95

Phe Val Arg Leu Val Arg Glu Ile Thr His Phe Tyr Ser Lys Glu Val
            100                 105                 110

Asn Arg Trp Thr Pro Glu Ala Leu Val Ala Ile Gln Glu Ala Ala Glu
        115                 120                 125

Thr His Met Ile Glu Met Phe Glu Asp Ala Tyr Leu Cys Ala Ile His
    130                 135                 140

Ala Lys Arg Val Thr Leu Met Gln Lys Asp Ile His Leu Ala Arg Arg
145                 150                 155                 160

Ile Gly Gly Arg Arg His Trp
                165

<210> SEQ ID NO 29
<211> LENGTH: 504
<212> TYPE: DNA
<213> ORGANISM: Musa acuminata
```

-continued

```
<400> SEQUENCE: 29
atggcgagaa cgaagcatct gtccaacagg tcctcctctc gccctcggaa gcgcttccat      60
ttcggtcggt ctccagggca gcgaacccccc gctgatgcga atcggcctgc gacgccatct     120
ggtgctactc ctagaaccac ggccaccaga tcgagggata cgcctcaagg ggcaccgagc     180
caatcaaaac agcagccgag gcggcgcagg tttaggccgg gggtggtggc gctacgcgag     240
atcaggaatt tgcagaagac gtggaatcta ttgatccctt tcgctccgtt tgtcagactt     300
gttcgggaga tcactcattt ctactcgaaa gaagtaaacc gatggacccc tgaagcttta     360
gttgcgattc aagaggcagc ggaaactcat atgatagaaa tgtttgaaga tgcatatctc     420
tgtgcaattc atgcaaaacg tgttaccctt atgcaaaaag atatccatct agcaaggcga     480
ataggaggaa gaagacattg gtga                                            504
```

```
<210> SEQ ID NO 30
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 30
gcgcccagct gttcgacctg                                                  20
```

```
<210> SEQ ID NO 31
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 31
gctcgtggag aacaacctga                                                  20
```

```
<210> SEQ ID NO 32
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 32
ggaaggcgag aagcgctgcg                                                  20
```

```
<210> SEQ ID NO 33
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 33
gtacggctgc gataccggcg                                                  20
```

```
<210> SEQ ID NO 34
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 34
gtcgccaact gctatctccg                                                  20
```

```
<210> SEQ ID NO 35
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 35
ggatactaca accagtacag                                                              20

<210> SEQ ID NO 36
<211> LENGTH: 19
<212> TYPE: DNA
<213> ORGANISM: Artificial Sequence
<220> FEATURE:
<223> OTHER INFORMATION: synthetic polynucleotide

<400> SEQUENCE: 36
gtaaggtgct ggagaatcg                                                               19

<210> SEQ ID NO 37
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 37
gctttgacga ggcagagctt                                                              20

<210> SEQ ID NO 38
<211> LENGTH: 70
<212> TYPE: DNA
<213> ORGANISM: Artificial Sequence
<220> FEATURE:
<223> OTHER INFORMATION: synthetic polynucleotide

<400> SEQUENCE: 38
cgcggaaggc gagaagcgct gcgcggtcgg tggaggcagg gactgcaggt tgggtcgccg     60
acgccaggac                                                                        70

<210> SEQ ID NO 39
<211> LENGTH: 58
<212> TYPE: DNA
<213> ORGANISM: Artificial Sequence
<220> FEATURE:
<223> OTHER INFORMATION: synthetic polynucleotide

<400> SEQUENCE: 39
cgcggaaggc gagaagtgcg cggtcggtgg aggcagggac tgcaggttgg gtcgccga      58

<210> SEQ ID NO 40
<211> LENGTH: 60
<212> TYPE: DNA
<213> ORGANISM: Artificial Sequence
<220> FEATURE:
<223> OTHER INFORMATION: synthetic polynucleotide

<400> SEQUENCE: 40
tccgtacggc tgcgataccg gcggggatct cgccggagaa gcggttgtgg gagaggtcga    60

<210> SEQ ID NO 41
<211> LENGTH: 58
<212> TYPE: DNA
```

-continued

<210> ORGANISM: Artificial Sequence
<220> FEATURE:
<223> OTHER INFORMATION: synthetic polynucleotide

<400> SEQUENCE: 41
tccgtacggc tgcgatacgc ggggatctcg ccggagaagc ggttgtggga gaggtcga        58

<210> SEQ ID NO 42
<211> LENGTH: 59
<212> TYPE: DNA
<213> ORGANISM: Artificial Sequence
<220> FEATURE:
<223> OTHER INFORMATION: synthetic polynucleotide

<400> SEQUENCE: 42
tccgtacggc tgcgataccg cggggatctc gccggagaag cggttgtggg agaggtcga       59

<210> SEQ ID NO 43
<211> LENGTH: 266
<212> TYPE: DNA
<213> ORGANISM: Artificial Sequence
<220> FEATURE:
<223> OTHER INFORMATION: synthetic polynucleotide

<400> SEQUENCE: 43
tccgtacggc tgcgataccg gcggggatct cgccggagaa gcggttgtgg gagaggtcga      60
ggaggaggag agcggagttg tcggggtcgg cgacgatccg cggcgggacg cgccggaga      120 agcggttgtg ggagaggtcg aggaggagga gagcggagtt gtcggggtcg gcgacgatcc     180
gcggcgggac ggcgccggag atggcgttgc gggagagatc aagggcagcg aggcgcgcgg     240
ggaaggagag acgcggggag agcggg                                          266

<210> SEQ ID NO 44
<211> LENGTH: 61
<212> TYPE: DNA
<213> ORGANISM: Artificial Sequence
<220> FEATURE:
<223> OTHER INFORMATION: synthetic polynucleotide

<400> SEQUENCE: 44
gtcggatact acaaccagta cagcggcggg gtcccgcgcg agttcggcgc gctccagtcg      60
c                                                                       61

<210> SEQ ID NO 45
<211> LENGTH: 60
<212> TYPE: DNA
<213> ORGANISM: Artificial Sequence
<220> FEATURE:
<223> OTHER INFORMATION: synthetic polynucleotide

<400> SEQUENCE: 45
gtcggatact acaaccagtc agcggcgggg tcccgcgcga gttcggcgcg ctccagtcgc      60

<210> SEQ ID NO 46
<211> LENGTH: 61
<212> TYPE: DNA
<213> ORGANISM: Artificial Sequence
<220> FEATURE:
<223> OTHER INFORMATION: synthetic polynucleotide

<400> SEQUENCE: 46
ctggcttgac gaggcagagc ttaggagcta cacatcagtc atccatgcta atgtgtatca      60
g                                                                       61

-continued

```
<210> SEQ ID NO 47
<211> LENGTH: 60
<212> TYPE: DNA
<213> ORGANISM: Artificial Sequence
<220> FEATURE:
<223> OTHER INFORMATION: synthetic polynucleotide

<400> SEQUENCE: 47
ctggcttgac gaggcagact taggagctac acatcagtca tccatgctaa tgtgtatcag        60
```